(12) United States Patent
Kurosawa et al.

(10) Patent No.: US 9,593,165 B2
(45) Date of Patent: *Mar. 14, 2017

(54) ANTIBODY CAPABLE OF SPECIFICALLY RECOGNIZING TRANSFERRIN RECEPTOR

(71) Applicants: UNIVERSITY OF MIYAZAKI, Miyazaki-shi, Miyazaki (JP); PERSEUS PROTEOMICS INC., Tokyo (JP)

(72) Inventors: Yoshikazu Kurosawa, Nagoya (JP); Kazuhiro Morishita, Miyazaki (JP); Lilin Zhang, Tokyo (JP); Gene Kurosawa, Tokyo (JP); Katsuyuki Mitomo, Tokyo (JP); Yukio Sudo, Tokyo (JP); Fumiko Nomura, Tokyo (JP); Yoshinori Ukai, Tokyo (JP)

(73) Assignees: UNIVERSITY OF MIYAZAKI, Miyazaki-Shi (JP); PERSEUS PROTEOMICS INC., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/441,307

(22) PCT Filed: Nov. 8, 2013

(86) PCT No.: PCT/JP2013/080249
§ 371 (c)(1),
(2) Date: May 7, 2015

(87) PCT Pub. No.: WO2014/073641
PCT Pub. Date: May 15, 2014

(65) Prior Publication Data
US 2015/0291697 A1    Oct. 15, 2015

(30) Foreign Application Priority Data

Nov. 8, 2012 (JP) ................................ 2012-246215

(51) Int. Cl.
| | | |
|---|---|---|
| C12P 21/04 | (2006.01) |
| C12P 21/06 | (2006.01) |
| C12N 5/00 | (2006.01) |
| C07H 21/04 | (2006.01) |
| C07K 16/00 | (2006.01) |
| C07K 16/28 | (2006.01) |
| C07K 16/30 | (2006.01) |
| A61K 39/00 | (2006.01) |

(52) U.S. Cl.
CPC .......... *C07K 16/2881* (2013.01); *C07K 16/30* (2013.01); *A61K 2039/505* (2013.01); *C07K 2317/14* (2013.01); *C07K 2317/21* (2013.01); *C07K 2317/565* (2013.01); *C07K 2317/567* (2013.01); *C07K 2317/622* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| 5,585,089 A | 12/1996 | Queen et al. |
| 5,667,781 A | 9/1997 | Trowbridge et al. |
| 7,976,841 B2 | 7/2011 | Monteiro et al. |
| 2009/0053243 A1 | 2/2009 | Kurosawa et al. |
| 2009/0203538 A1 | 8/2009 | Sugioka et al. |
| 2011/0256156 A1 | 10/2011 | Chatterton et al. |
| 2012/0046451 A1 | 2/2012 | Kurosawa et al. |
| 2013/0045206 A1 | 2/2013 | Poul et al. |
| 2014/0114054 A1 | 4/2014 | Kurosawa et al. |

FOREIGN PATENT DOCUMENTS

| CN | 101245107 A | 8/2008 |
| CN | 102741282 A | 10/2012 |
| EP | 0125023 B1 | 6/1991 |
| EP | 0120694 B1 | 7/1993 |
| GB | 2188638 A | 10/1987 |
| JP | 2005-185281 A | 7/2005 |
| JP | 4870348 B2 | 2/2012 |
| JP | 2013-194043 A | 9/2013 |
| WO | WO 92/01047 A1 | 1/1992 |
| WO | WO 92/03918 A1 | 3/1992 |
| WO | WO 92/20791 A1 | 11/1992 |
| WO | WO 93/06213 A1 | 4/1993 |
| WO | WO 93/11236 A1 | 6/1993 |

(Continued)

OTHER PUBLICATIONS

Daniels et al. 2012. BBA. 1820:291-317.*
Beguin et al., "Soluble CD23 and Other Receptors (CD4, CD8, CD25, CD71) in Serum of Patients with Chronic Lymphocytic Leukemia," Leukemia, vol. 7, No. 12, Dec. 1993, pp. 2019-2025 (10 pages total).
Berinstein et al., "Association of serum Rituximab (IDEC-C2B8) concentration and anti-tumor response in the treatment of recurrent low-grade or follicular non-Hodgkin's lymphoma," Annals of Oncology, vol. 9, 1998, pp. 995-1001.
Brooks et al., "Phase Ia Trial of Murine Immunoglobulin A Antitransferrin Receptor Antibody 42/6," Clinical Cancer Research, vol. 1, Nov. 1995, pp. 1259-1265.
Brüggemann et al., "Comparison of the Effector Functions of Human Immunoglobulins Using a Matched Set of Chimeric Antibodies," Journal of Experimental Medicine, vol. 166, Nov. 1987, pp. 1351-1361.
Brüggemann et al., "The Immunogenicity of Chimeric Antibodies," Journal of Experimental Medicine, Brief Definitive Report, vol. 170, Dec. 1989, pp. 2153-2157.

(Continued)

*Primary Examiner* — Shulamith H Shafer
(74) *Attorney, Agent, or Firm* — Birch, Stewart, Kolasch & Birch, LLP

(57) ABSTRACT

The present invention provides an antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 7, respectively, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively.

20 Claims, 7 Drawing Sheets

(56) References Cited

FOREIGN PATENT DOCUMENTS

| WO | WO 93/12227 A1 | 6/1993 |
|---|---|---|
| WO | WO 93/19172 A1 | 9/1993 |
| WO | WO 94/02602 A1 | 2/1994 |
| WO | WO 94/25585 A1 | 11/1994 |
| WO | WO 95/01438 A1 | 1/1995 |
| WO | WO 96/33735 A1 | 10/1996 |
| WO | WO 96/34096 A1 | 10/1996 |
| WO | WO 2006/090750 A1 | 8/2006 |
| WO | WO 2008/007648 A1 | 1/2008 |
| WO | WO 2011/073943 A1 | 6/2011 |
| WO | WO 2012/153707 A1 | 11/2012 |
| WO | WO 2013/031619 A1 | 3/2013 |

OTHER PUBLICATIONS

Courtenay-Luck et al., "Development of Primary and Secondary Immune Responses to Mouse Monoclonal Antibodies Used in the Diagnosis and Therapy of Malignant Neoplasms," Cancer Research, vol. 46, Dec. 1986, pp. 6489-6493.

Dillman et al., "Therapy of Chronic Lymphocytic Leukemia and Cutaneous T-Cell Lymphoma With T101 Monoclonal Antibody," Journal of Clinical Oncology, vol. 2, No. 8, Aug. 1984, pp. 881-891.

Galbraith et al., "Transferrin Binding to Peripheral Blood Lymphocytes Activitated by Phytohemagglutinin Involves a Specific Receptor," Journal of Clinical Investigation, vol. 66, Nov. 1980, pp. 1135-1143.

Gao et al., "De novo identification of tumor-specific internalizing human antibody-receptor pairs by phage-display methods," Journal of Immunological Methods, vol. 274, 2003, pp. 185-197.

Gupta et al., "Correlation of Transferrin Receptor Expression with Histologic Grade and Immunophenotype in Chronic Lymphocytic Leukemia and Non-Hodgkin's Lymphoma," Hematologic Pathology, vol. 4, No. 1, 1990, pp. 37-41 (7 pages total).

Habeshaw et al., "Correlation of Transferrin Receptor Expression with Histological Class and Outcome in Non-Hodgkin Lymphoma," The Lancet, Mar. 5, 1983, pp. 498-501.

Houghton et al., "Mouse monoclonal IgG3 antibody detecting GD3 ganglioside: A phase I trial in patients with malignant melanoma," Proceedings of the National Academy of Sciences USA, vol. 82, Feb. 1985, pp. 1242-1246.

International Preliminary Report on Patentability and Written Opinion of the International Searching Authority (Forms PCT/IB/338, PCT/IB/373, PCT/ISA/237 and PCT/IB/326) for International Application No. PCT/JP2013/080249, dated May 21, 2015, with an English translation.

International Search Report (Form PCT/ISA/210) for International Application No. PCT/JP2013/080249, dated Jan. 21, 2014.

Jandl et al., "The Plasma-to-Cell Cycle of Transferrin," Journal of Clinical Investigation, vol. 42, No. 3, 1963, pp. 314-326.

Keer et al., "Elevated Transferrin Receptor Content in Human Prostate Cancer Cell Lines Assessed In Vitro and In Vivo," The Journal of Urology, vol. 143, No. 2, Feb. 1990, pp. 381-385 (9 pages total).

Khazaeli et al., "Phase I Trial of Multiple Large Doses of Murine Monoclonal Antibody CO17-1A. II. Pharmacokinetics and Immune Response," Journal of the National Cancer Institute, vol. 80, No. 12, Aug. 17, 1988, pp. 937-942.

Lloyd et al., "Demonstration of an epitope of the transferrin receptor in human cervical epithelium—a potentially useful cell marker," Journal of Clinical Pathology, vol. 37, 1984, pp. 131-135.

Lobuglio et al., "Phase I Trial of Multiple Large Doses of Murine Monoclonal Antibody CO17-1A. I. Clinical Aspects," Journal of the National Cancer Institute, vol. 80, No. 12, Aug. 17, 1988, pp. 932-936 (10 pages total).

Loh et al., "Transferrin Receptors on the Human Placental Microvillous Membrane," Journal of Clinical Investigation, vol. 65, May 1980, pp. 1182-1191.

Loos, "The Classical Complement Pathway: Mechanism of Activation of the First Component by Antigen-Antibody Complexes," Progress in Allergy, vol. 30, 1982, pp. 135-192 (64 pages total).

Mass et al., "The Concordance Between the Clinical Trials Assay (CTA) and Fluorescence in Situ Hybridization (FISH) in the Herceptin Pivotal Trials," Program/Proceedings of the Thirty-Sixth Annual Meeting of the American Society of Clinical Oncology, May 20-23, 2000, p. 75a (5 pages total).

Meeker et al., "A Clinical Trial of Ariti-Idiotype Therapy for B Cell Malignancy," Blood, vol. 65, No. 6, Jun. 1985, pp. 1349-1363.

Moura et al., "A neutralizing monoclonal antibody (mAb A24) directed against the transferrin receptor induces apoptosis of tumor T lymphocytes from ATL patients," Blood, vol. 103, No. 5, Mar. 1, 2004, pp. 1838-1845.

Niitsu et al., "Transferrin Receptors in Human Cancerous Tissues," Tohoku Journal of Experimental Medicine, vol. 153, 1987, pp. 239-243.

Pimm et al., "The Characteristics of Blood-Borne Radiolabels and the Effect of Anti-Mouse IgG Antibodies on Localization of Radiolabeled Monoclonal Antibody in Cancer Patients," Journal of Nuclear Medicine, vol. 26, No. 9, Sep. 1985, pp. 1011-1023.

Poul et al., "Selection of Tumor-Specific Internalizing Human Antibodies from Phage Libraries," Journal of Molecular Biology, vol. 301, 2000, pp. 1149-1161.

Prior et al., "Transferrin receptor expression in tumours of the human nervous system: relation to tumour type, grading and tumour growth fraction," Virchows Archiv A Pathological Anatomy and Histopathology, vol. 416, No. 6, Apr. 1990, pp. 491-496 (9 pages total).

Prost et al., "Differential transferrin receptor density in human colorectal cancer: A potential probe for diagnosis and therapy," International Journal of Oncology, vol. 13, No. 4, Oct. 1998, pp. 871-875 (9 pages total).

Riechmann et al., "Reshaping human antibodies for therapy," Nature, Articles, vol. 332, Mar. 24, 1988, pp. 323-327.

Ritter et al., "Serological Analysis of Human Anti-Human Antibody Responses in Colon Cancer Patients Treated with Repeated Doses of Humanized Monoclonal Antibody A33," Cancer Research, vol. 61, Sep. 15, 2001, pp. 6851-6859.

Ryschich et al., "Transferrin receptor is a marker of malignant phenotype in human pancreatic cancer and in neuroendocrine carcinoma of the pancreas," European Journal of Cancer, vol. 40, 2004 (Available online Apr. 17, 2004), pp. 1418-1422.

Sciot et al., "Transferrin receptor expression in human hepatocellular carcinoma: an immunohistochemical study of 34 cases," Histopathology, vol. 12, No. 1, Jan. 1988, pp. 53-63 (14 pages total).

Seymour et al., "Transferrin Receptor Expression by Human Bladder Transitional Cell Carcinomas," Urological Research, vol. 15, 1987, pp. 341-344.

Shawler et al., "Human Immune Response to Multiple Injections of Murine Monoclonal IgG," The Journal of Immunology, vol. 135, No. 2, Aug. 1985, pp. 1530-1535.

Shindelman et al., "Demonstration of the Transferrin Receptor in Human Breast Cancer Tissue. Potential Marker for Identifying Dividing Cells," International Journal of Cancer, vol. 27, 1981, pp. 329-334.

Smith et al., "Transferrin Receptor Expression in Primary Superficial Human Bladder Tumours Identifies Patients who Develop Recurrences," British Journal of Urology, vol. 65, No. 4, Apr. 1990, pp. 339-344 (10 pages total).

Szolar et al., "Qualification and application of a surface plasmon resonance-based assay for monitoring potential HAHA responses induced after passive administration of a humanized anti . . . ," Journal of Pharmaceutical and Biomedical Analysis, vol. 41, 2006 (online Apr. 27, 2006), pp. 1347-1353.

Taetle et al., "Mechanisms of Growth Inhibition by Anti-Transferrin Receptor Monoclonal Antibodies," Cancer Research, vol. 46, Apr. 1986, pp. 1759-1763.

Trowbridge et al., "Monoclonal antibody to transferrin receptor blocks transferrin binding and inhibits human tumor cell growth in vitro," Proceedings of the National Academy of Sciences USA, vol. 79, Feb. 1982, pp. 1175-1179.

Tschopp, "Kinetics of Activation of the First Component of Complement (C1) by IgG Oligomers," Molecular Immunology, vol. 19, No. 5, 1982, pp. 651-657.

(56) References Cited

OTHER PUBLICATIONS

Vanderpuye et al., "Transferrin Receptors in the Basal Plasma Membrane of the Human Placental Syncytiotrophoblast," Placenta, vol. 7, 1986, pp. 391-403.
White et al., "Combinations of Anti-Transferrin Receptor Monoclonal Antibodies Inhibit Human Tumor Cell Growth in Vitro and in Vivo: Evidence for Synergistic Antiproliferative Effects," Cancer Research, vol. 50, Oct. 1, 1990, pp. 6295-6301.
Yanagihara et al., "Effects of epidermal growth factor, transferrin, and insulin on lipofection efficiency in human lung carcinoma cells," Cancer Gene Therapy, vol. 7, No. 1, 2000, pp. 59-65.
Extended European Search Report for Appl. No. 13853637.0 dated Jun. 1, 2016.
Chinese Office Action for Appl. No. 201380058622.3 dated Dec. 5, 2016 (w/ English translation).

\* cited by examiner

Figure 3

```
                                 *****              ****************
TfR006VH    QVQLVQSGGGVVQPGRSLRLSCAASGFPFKSYGMHWVRQAPGKGLEWVAVISFDGSSKYYADSVKG
                |                        |                  | |
IGHV3-30    QVQLVESGGGVVQPGRSLRLSCAASGFTFSSYGMHWVRQAPGKGLEWVAVISYDGSNKYYADSVKG
                | |   |    |             |  ||              |  | ||
humIII VH   EVQLVESGGGLVQPGGSLRLSCAASGFTFSSYAMSWVRQAPGKGLEWVSVISGDGGSTYYADSVKG

*************
TfR006VH    RFTISRDNSKNTLYLQMNSLRGEDTAVYYCARDSNFWSGYYSPVDVWGQGTTVTVSS
                                       |
IGHV3-30    RFTISRDNSKNTLYLQMNSLRAEDTAVYYCAR
                                       |
humIIIVH    RFTISRDNSKNTLYLQMNSLRAEDTAVYYCARGF          DYWGQGTLVTVSS
```

ANTIBODY CAPABLE OF SPECIFICALLY RECOGNIZING TRANSFERRIN RECEPTOR

TECHNICAL FIELD

The present invention relates to an anti-TfR antibody specifically reacting with a human TfR antigen. In addition, the present invention relates to a pharmaceutical composition comprising the anti-TfR antibody, and particularly to a pharmaceutical composition associated with the treatment of malignant tumor.

BACKGROUND ART

Cancer is the first cause of death in Japan, and with aging, the number of patients suffering from cancer has been increasing year by year. Thus, it has been strongly desired to develop a drug or a treatment method, which is highly effective and highly safe. Conventional chemotherapy, radiotherapy and the like have been problematic in that they cause damage to normal cells as well as killing cancer cells, and they cause strong side effects. In order to solve this problem, studies have been intensively conducted regarding molecularly targeted therapy, in which a drug targeting a molecule that is expressed specifically in a cancer cell is designed, and the therapy is carried out using the drug. Among such molecularly targeted cancer therapeutic agents, antibody drugs have attracted considerable attention because they are advantageous in terms of their long half-life and a few side effects. Examples of successfully developed cancer therapeutic agents include a chimeric antibody Rituxan that targets CD20 (Non Patent Literature 1), a humanized antibody Herceptin that targets Her2/neu (Non Patent Literature 2), and a humanized antibody Avastin that targets a vascular endothelial growth factor (VEGF). These antibodies have been used for cancer as a target disease, and their therapeutic effects have been recognized.

Antibodies which are used as therapeutic agents are divided into non-labeled antibodies and labeled antibodies. The action mechanisms of such non-labeled antibodies are considered to be: (1) antibody-dependent cellular cytotoxicity (ADCC) (Non Patent Literature 3) or complement-dependent cytotoxicity (CDC) (Non Patent Literature 4), which are associated with immunocytes or molecules; (2) inhibition of signals associated with intracellular survival or growth by target molecules; (3) induction of apoptosis; and (4) regulation of secretion of cytokines. By combining these mechanisms, the non-labeled antibody kills tumor cells or terminates the growth thereof, so as to exhibit its therapeutic effects. On the other hand, a labeled antibody is formed by linking a radioactive substance or a cytotoxic substance such as a toxin, an enzyme or a drug to an antibody, and the specificity of the antibody is utilized to deliver such a substance only to cancer tissues, so as to achieve the improvement of therapeutic effects and reduction in side effects.

A transferrin receptor (TfR) was at first identified as a receptor that is present on a reticulocyte as a cell membrane structure for incorporating transferrin (Tf)-bound iron into a cell (Non Patent Literature 5). Thereafter, it was discovered that the transferrin receptor (TfR) is expressed in placental trophoblasts (Non Patent Literatures 10 to 12), in activated lymphocytes (Non Patent Literature 12), and further, in various tumor cells. It has been reported that the transferrin receptor (TfR) is expressed at a high level, for example, in breast cancer (Non Patent Literature 6), prostate cancer (Non Patent Literature 7), lung cancer (Non Patent Literature 8), pancreatic cancer (Non Patent Literature 9), colon cancer (Non Patent Literatures 30 and 31), stomach cancer (Non Patent Literature 31), bladder cancer (Non Patent Literatures 32 and 33), hepatic cancer (Non Patent Literature 34), cervical cancer (Non Patent Literature 35), brain tumor (Non Patent Literature 36), chronic lymphocytic leukemia (Non Patent Literatures 37 and 38), non-Hodgkin's lymphoma (Non Patent Literatures 38 and 39), and adult T-cell leukemia (Non Patent Literature 40). Moreover, since TIER is expressed on the surface of various types of cancer cells at a high level and is expressed in normal cells at a low level, this receptor had been recognized as a molecular target for cancer therapy from long ago (Non Patent Literatures 13 to 16, and Patent Literatures 1 and 2). However, previously developed anti-human TfR antibodies were all derived from animals, and further, they did not have a significant tumor growth-inhibiting effect. It has been generally known that when an antibody derived from an animal other than a human, such as a mouse antibody, is administered to a human, the administered antibody is recognized as a foreign matter, so that a human antibody against the mouse antibody (Human Anti Mouse Antibody: hereinafter referred to as HAMA) is induced in the human body. It has been known that the HAMA reacts with the administered mouse antibody, and causes side effects (Non Patent Literatures 17 to 20) or accelerates the disappearance of the administered mouse antibody from the body (Non Patent Literatures 18, 21 and 22), thereby reducing the therapeutic effects of the mouse antibody (Non Patent Literatures 23 and 24). In fact, a phase 1 clinical testing was carried out using a certain mouse anti-human TfR antibody. As a result, generation of HAMA was observed, and significant therapeutic effects were not found (Non Patent Literature 25).

In order to avoid such a problem, a chimeric antibody was developed (Patent Literatures 3 and 4). The chimeric antibody comprises portions of two or more species-derived antibodies (a variable region of mouse antibody and a constant region of human antibody, etc.). Such a chimeric antibody is advantageous in that while it retains the characteristics of a mouse antibody, it has human Fc and thus it is able to stimulate a human complement or cytotoxicity. However, such a chimeric antibody still provokes a "human anti-chimeric antibody," namely HACA (Human Anti-Chimera Antibody) response (Non Patent Literature 26). Moreover, a recombinant antibody, in which only a portion of a substituted antibody is a complementarity determining region (that is, "CDR") was developed (Patent Literatures 5 and 6). Using a CDR transplantation technique, an antibody consisting of a mouse CDR, and human variable region framework and constant region, namely, "humanized antibody" was prepared (Non Patent Literature 27). However, even such a humanized antibody has immunogenicity to humans, and thus, causes a HAHA (Human Anti-Human Antibody) reaction (Non Patent Literatures 28 and 29). Accordingly, it has been desired to develop a more safe and effective antibody therapeutic drug having no immunogenicity, which can be applied to clinical sites.

Furthermore, in order to overcome the immunogenicity of a therapeutic antibody, a method for producing a complete human antibody has also been developed. For example, a desired human antibody can be obtained by immunizing a transgenic animal having all repertoire of human antibody genes with a desired antigen (Patent Literatures 7 to 12). In addition, a technique of obtaining a human antibody by panning a human antibody library has been known. For example, a variable region of a human antibody is allowed to express as a single-chain antibody (scFv) on the surface of a phage by phage display method, and a phase binding to an antigen can be then selected. By analyzing the gene of the selected phage, a DNA sequence encoding the variable region of a human antibody binding to the antigen can be determined. An expression vector that is more suitable for the DNA sequence of the scFv is constructed, and a complete human antibody can be obtained (Patent Literatures 13-18). By such a phage display method applied to the human antibody scFv, a human anti-TfR phage antibody has been obtained (Patent Literature 20). By the way, it is important for the discovery of antibody drugs to obtain an antibody that recognizes a "native form" target cancer antigen that is present on the surface of a cell membrane, and the pharmacological effect of the obtained antibody is different depending on a panning method or a difference in screening. The present inventors have produced so far an enormous human antibody library consisting of a hundred billion independent clones, and have established a comprehensive method for obtaining antibodies against proteins existing on the cancer cell membrane surface (cell surface antigens) by an original technique using several tens types of cancer cells (Patent Literature 19).

PRIOR ART LITERATURES

Patent Literature

Patent Literature 1: U.S. Pat. No. 5,667,781
Patent Literature 2: U.S. Pat. No. 7,976,841
Patent Literature 3: European Patent No. 120694
Patent Literature 4: European Patent No. 125023
Patent Literature 5: U. K. Patent No. GB2188638A
Patent Literature 6: U.S. Pat. No. 5,585,089
Patent Literature 7: WO 93/12227
Patent Literature 8: WO 1992/03918
Patent Literature 9: WO 1994/02602
Patent Literature 10: WO 1994/25585,
Patent Literature 11: WO 1996/34096,
Patent Literature 12: WO 1996/33735
Patent Literature 13: WO 1992/01047
Patent Literature 14: WO 1992/20791,
Patent Literature 15: WO 1993/06213
Patent Literature 16: WO 1993/11236
Patent Literature 17: WO 1993/19172
Patent Literature 18: WO 1995/01438
Patent Literature 19: Japanese Patent No. 4870348
Patent Literature 20: WO 2011/073943

Non Patent Literature

Non Patent Literature 1: Mass R, et al., Proc Am Soci Clin Oncol 19, 75a, 2000
Non Patent Literature 2: Berinstein N L, et al., Annals of Oncology 1998, 9: 995-1001.
Non Patent Literature 3: Bruggemann M., et al., J. Exp. Med., 166, 1351-1361.
Non Patent Literature 4: Loos M. (1982). Prog. Allergy, 30, 135-192. Mol Immunol. 1982 May; 19(5): 651-7.
Non Patent Literature 5: J Clin Invest 1963; 42, 314-326
Non Patent Literature 6: Int J Cancer 1981; 27: 329-334,
Non Patent Literature 7: J Urol 1990; 143: 381-385,
Non Patent Literature 8: Cancer Gene Ther 2000; 7: 59-65;
Non Patent Literature 9: Eur J Cancer 2004; 40 (9): 1418-1422
Non Patent Literature 10: J Clin Invest 1980; 65: 1182-1191.
Non Patent Literature 11: Placenta 1986; 7: 391-403
Non Patent Literature 12: J Clin Invest (1980) 66, 1135-1143.10
Non Patent Literature 13: Proc. Natl Acad Sci USA 1982; 79: 1175-1179,
Non Patent Literature 14: Cancer Res 1986; 46: 1759-1763,
Non Patent Literature 15: Cancer Res 1990; 50: 6295-6301,
Non Patent Literature 16: Blood 2004; 103: 1838-1845
Non Patent Literature 17: J. Clin. Oncol., 2,881 (1984)
Non Patent Literature 18: Blood, 65, 1349 (1985)
Non Patent Literature 19: J. Natl. Cancer Inst., 80, 932 (1988)
Non Patent Literature 20: Proc. Natl. Acad. Sci., U.S.A., 82, 1242 (1985)
Non Patent Literature 21: J. Nucl. Med., 26, 1011(1985)
Non Patent Literature 22: J. Natl. Cancer Inst., 80, 937 (1988)
Non Patent Literature 23: J. Immunol., 135, 1530 (1985)
Non Patent Literature 24: Cancer Res., 46, 6489 (1986)
Non Patent Literature 25: Clini. Cancer. Res. 1995; 1: 1259-1265
Non Patent Literature 26: J. Exp. Med., 170, 2153-2157, 1989
Non Patent Literature 27: Nature, 332, 323-327, 1988
Non Patent Literature 28: Cancer Res. 2001; 61: 6851-6859,
Non Patent Literature 29: J Pharm Biomed Anal. 2006; 41: 1347-1353
Non Patent Literature 30: Int J Oncol. 1998; 13(4): 871-5
Non Patent Literature 31: Tohoku J. exp. Med. 1987; 153: 239-243
Non Patent Literature 32: Urol. Res. 1987; 15: 341-344
Non Patent Literature 33: Br. J. Urol. 1990; 65: 339-344
Non Patent Literature 34: Histopathology 1988; 12: 53-63
Non Patent Literature 35: J. Clin. Pathol. 1984; 37: 131-135
Non Patent Literature 36: A Pathol. Anat. Histopathol. 1990; 416: 491-496
Non Patent Literature 37: Leukemia 1993; 7:2019-2025
Non Patent Literature 38: Hematol. Pathol. 1990; 4: 37-41
Non Patent Literature 39: Lancet 1983; 1: 498-501
Non Patent Literature 40: Blood 2004; 103: 1838-1845

SUMMARY OF INVENTION

Object to be Solved by the Invention

It is an object of the present invention to provide a complete human antibody having a strong tumor growth-inhibiting effect on TfR as a target. It is another object of the present invention to provide a method for producing the aforementioned antibody, and a therapeutic agent for disease such as cancer comprising the aforementioned antibody.

Means for Solving the Object

As mentioned above, an antibody that targets TfR had been developed as an antitumor agent. However, since this antibody had been derived from an animal, the development of an antibody therapeutic drug had not been successful due to generation of HAMA, insufficient drug effects, etc. Thus, the present inventors have conducted intensive studies regarding the original antibody production method described in Patent Literature 19, and as a result, they have obtained a phage antibody (scFv antibody) reacting with TfR existing on the cancer cell membrane, using human antibody library phage display. The inventors have modified such scFv antibodies to provide immunoglobulins, so as to prepare complete human IgG antibodies.

Furthermore, for the following purposes regarding the antibody, namely, for (1) the improvement of productivity, (2) the improvement of preservation stability, and (3) the improvement of antitumor effects, at least one amino acid of the CDR of the variable region of the obtained complete human anti-TfR antibody was modified, and optimization of the anti-TfR antibody was attempted for clinical application. As a result, it was found that the obtained mutant antibody reacts with human TfR at the same level as the parent strain and has a stronger antitumor effect. In particular, the antibody of the present invention obtained as described above was much more excellent than the human anti-TfR antibodies described in Patent Literature 20 and WO 2012/153707, in terms of tumor-inhibiting effect. Based on these findings, it was demonstrated that these antibodies are useful for the treatment of various cancers in which TfR is expressed at a high level, thereby completing the present invention.

Specifically, according to the present invention, antibodies specifically reacting human TfR, which are selected from the following (1) to (34), are provided.

(1) An antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 7, respectively, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively.

(2) An antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 8, respectively, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively.

(3) An antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 9, respectively, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively.

(4) An antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 10, respectively, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively.

(5) An antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 11, respectively, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively.

(6) An antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 12, respectively, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively.

(7) An antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 13, respectively, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively.

(8) An antibody, in which the heavy chain first complementarity determining region (VH CDR1), the heavy chain second complementarity determining region (VH CDR2), and the heavy chain third complementarity determining region (VH CDR3) are shown in SEQ 11) NOs: 1, 2, and 14, respectively, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively.

(9) An antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 15, respectively, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively.

(10) An antibody, in which the heavy chain has SEQ ID NO: 16, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively.

(11) An antibody, in which the heavy chain has SEQ ID NO: 17, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively.

(12) An antibody, in which the heavy chain has SEQ ID NO: 18, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively.

(13) An antibody, in which the heavy chain has SEQ ID NO: 19, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively.

(14) An antibody, in which the heavy chain has SEQ ID NO: 20, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively.

(15) An antibody, in which the heavy chain has SEQ ID NO: 21, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively.

(16) An antibody, in which the heavy chain has SEQ ID NO: 22, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively.

(17) An antibody, in which the heavy chain has SEQ ID NO: 23, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively.

(18) An antibody, in which the heavy chain has SEQ ID NO: 24, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively.

(19) An antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 3, respectively, and the light chain variable region is shown in SEQ ID NO: 25.

(20) An antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 3, respectively, and the light chain variable region is shown in SEQ ID NO: 26.

(21) An antibody, in which the heavy chain first complementarily determining region (VH CDR1), the heavy chain second complementarity determining region (VH CDR2), and the heavy chain third complementarity determining region (VH CDR3) are shown in SEQ ID NOs: 1, 2, and 3, respectively, and the light chain variable region is shown in SEQ ID NO: 28.

(22) An antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 3, respectively, and the light chain variable region is shown in SEQ ID NO: 29.

(23) An antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 3, respectively, and the light chain variable region is shown in SEQ ID NO: 31.

(24) An antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 3, respectively, and the light chain variable region is shown in SEQ ID NO: 32.

(25) An antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 3, respectively, and the light chain variable region is shown in SEQ ID NO: 34.

(26) An antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 3, respectively, and the light chain variable region is shown in SEQ ID NO: 36.

(27) An antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 3, respectively, and the light chain variable region is shown in SEQ ID NO: 37.

(28) An antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 3, respectively, and the light chain variable region is shown in SEQ ID NO: 38.

(29) An antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 3, respectively, and the light chain variable region is shown in SEQ ID NO: 40.

(30) An antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 3, respectively, and the light chain variable region is shown in SEQ ID NO: 41.

(31) An antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 3, respectively, and the light chain variable region is shown in SEQ ID NO: 42.

(32) An antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 52, 3, respectively, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively.

(33) An antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 53, 3, respectively, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively.

(34) An antibody; in which the heavy chain first complementarity determining region (VH CDR1), the heavy chain second complementarity determining region (VH CDR2), and the heavy chain third complementarity determining region (VH CDR3) are shown in SEQ ID NOs: 1, 54, 3, respectively, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively.

Preferably, the antibody of the present invention is a human antibody or a humanized antibody.

Preferably, the antibody of the present invention is an antibody fragment selected from the group consisting of Fab, Fab', F(ab)$_2$, a single-chain antibody (scFv), a dimerized V region (Diabody), a disulfide-stabilized V region (dsFv), and a peptide comprising CDR.

According to the present invention, DNA encoding the above-described antibody of the present invention is provided.

According to the present invention, a recombinant vector comprising the above-described DNA of the present invention is provided.

According to the present invention, a transformed cell line obtained by introducing the above-described recombinant vector of the present invention into a host cell is provided.

According to the present invention, a method for producing the antibody of the present invention, which comprises culturing the above-described transformed cell line of the present invention in a medium, then allowing the cell line to generate and accumulate the antibody of the present invention in the culture, and then collecting the antibody from the culture, is provided.

According to the present invention, a pharmaceutical composition comprising the above-described antibody of the present invention is provided.

According to the present invention, the above-described pharmaceutical composition, in which a cytotoxic substance binds to the antibody, is provided.

Preferably, the cytotoxic substance is a drug, a toxin, or a radioactive substance.

Preferably, the pharmaceutical composition of the present invention is used as an anticancer agent.

Preferably, the cancer is a solid cancer or a blood cancer.

Preferably, the solid cancer is lung cancer, colon cancer, stomach cancer, bladder cancer, pancreatic cancer, prostate cancer, hepatic cancer, cervical cancer, uterine cancer, ovarian cancer, breast cancer, head and neck cancer, or skin cancer.

Preferably, the blood cancer is leukemia, lymphoma, or myeloma.

More preferably, the blood cancer is adult T-cell leukemia (ATL).

According to the present invention, a method for inhibiting or treating cancer, which comprises administering the above-described antibody of the present invention to a subject, is further provided.

According to the present invention, use of the above-described antibody of the present invention for the production of a pharmaceutical composition or an anticancer agent is further provided.

Advantageous Effects of Invention

The antibody of the present invention is a complete human antibody, which specifically recognizes human TfR and inhibits the survival or growth of cancer cells that express TfR. When a human antibody is administered to a human, the antigenicity of the antibody is significantly reduced, and HAHA is not thereby generated. Hence, the human antibody can exhibit high antitumor action, causing a few side effects. That is to say, the anti-human TfR antibody of the present invention is useful as an anticancer agent.

BRIEF DESCRIPTION OF DRAWINGS

FIG. 3 shows an alignment of the VH amino acid sequence (SEQ ID NO: 43) of a TfR006 antibody, the amino acid sequence (SEQ ID NO: 44) of IGHV3-30, and the consensus amino acid sequence (SEQ ID NO: 45) of human germline gene subgroup III.

EMBODIMENTS FOR CARRYING OUT THE INVENTION

Figure 1:
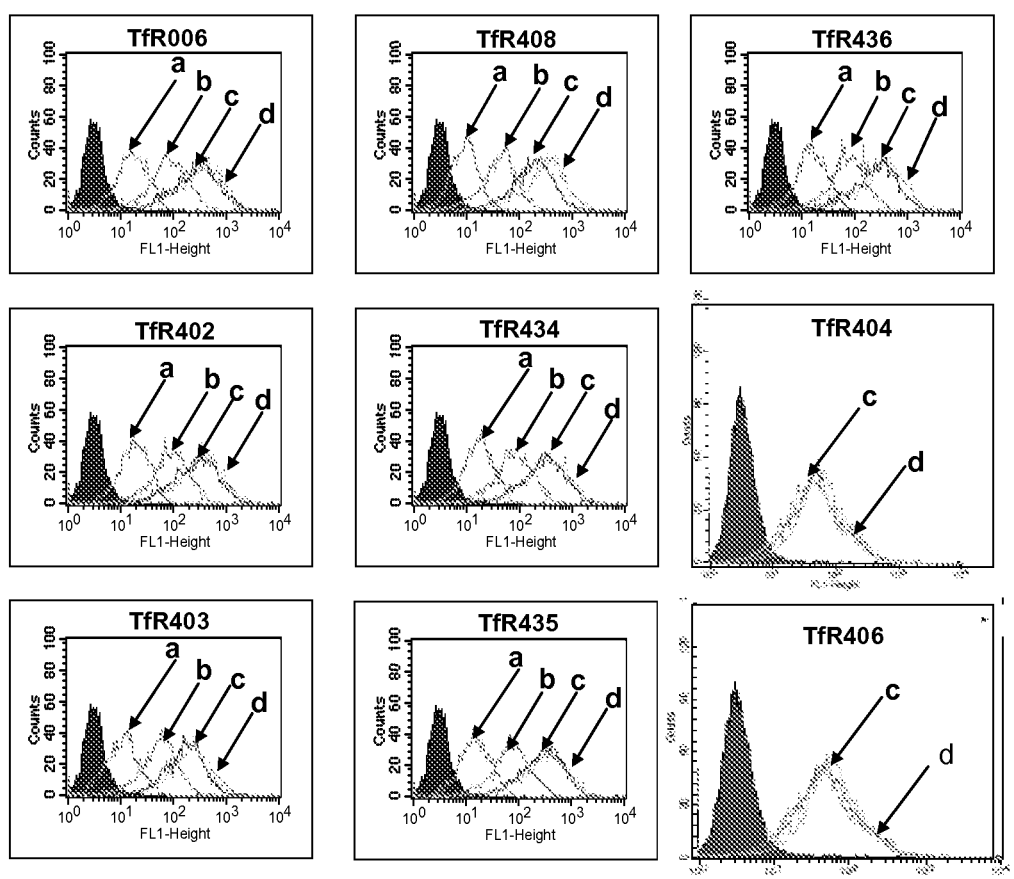
FIG. 1 shows the results of flow cytometry using the reaction of each modified anti-TfR006 antibodies with the leukemia cell line K562.

Hereinafter, the present invention will be described more in detail.

Definitions and General Techniques

Unless otherwise specified in the present description, scientific terms used regarding the present invention have meanings that are generally understood by a person skilled in the art. In general, nomenclatures and techniques applied to the cell and tissue culture, molecular biology, immunology, microbiology, genetics, protein and nucleic acid chemistry, and hybridization, which are described in the present description, are well known in the present technical field, and thus, are commonly used.

The methods and techniques of the present invention are carried out in accordance with conventional methods that are well known in the present technical field, in such ways as described in a variety of general reference documents cited and discussed throughout the present description and more specific reference documents, unless otherwise specified.

TfR

Human transferrin receptor (TfR) is a single-pass transmembrane protein (SEQ ID NO: 51) comprising 760 amino acids, and it is encoded by human chromosome 3. This protein has also been known as a CD71 antigen, and it is considered that this protein is associated with incorporation of iron into cells and cell growth. The TfR of the present invention is not particularly limited in terms of structure. Thus, human TfR includes all of a monomer, a polymer, an intact form expressed on a cell membrane, a soluble form constituted in an extracellular region, a truncated form, a mutation form caused by genetic mutation, deletion, etc., and a form that has undergone posttranslational modification by phosphorylation or the like.

React and Reactivity

The terms "react" and "reactivity" have the same meanings in the present description, unless otherwise specified. That is, these terms mean that an antibody recognizes an antigen. The antigen used herein may be any of an intact TfR expressed on a cell membrane, a truncated form, and a soluble form. In addition, the antigen may be either a TfR having a three-dimensional structure or a denatured TfR. Examples of a means for examining reactivity include flow cytometry (FACS), enzyme-linked immunosorbent assay (ELISA), Western blotting, microfluorescence measuring technique (FMAT), surface plasmon resonance (Biacore), immunostaining, and immunoprecipitation.

The antibody used in flow cytometry may be either an antibody labeled with a fluorescent substance such as FITC or with biotin, or an unlabeled antibody. A fluorescently-labeled avidin, a fluorescently-labeled anti-human immunoglobulin antibody, or the like is used, depending on the presence or absence of labeling of the antibody used and the type thereof. Reactivity can be evaluated by adding a sufficient amount of anti-TfR antibody (generally having a final concentration of 0.01 to 10 µg/mL) to an analyte, and then by comparing the obtained reactivity with the reactivity with a negative control antibody or a positive control antibody.

Antibody

In the present description, the following abbreviations (in the parentheses) are used in accordance with the customs, as necessary.

Heavy chain (H chain), light chain (L chain), heavy chain variable region (VH), light chain variable region (VL), complementarity determining region (CDR), first complementarity determining region (CDR1), second complementarity determining region (CDR2), third complementarity determining region (CDR3), heavy chain first complementarity determining region (VH CDR1), heavy chain second complementarity determining region (VH CDR2), heavy chain third complementarity determining region (VH CDR3), light chain first complementarity determining region (VL CDR1), light chain second complementarity determining region (VL CDR2), and light chain third complementarity determining region (VL CDR3).

In the present description, the term "antibody" has the same definitions as immunoglobulin, and should be understood as generally known in the present technical field. Specifically, the term "antibody" is not limited by any given specific method for producing the antibody. For example, the term "antibody" includes, but is not limited to, a recombinant antibody, a monoclonal antibody, and a polyclonal antibody.

In the present description, the term "human antibody is used to mean any given antibody, in which the sequences of a variable region and a constant region are human sequences. This term includes antibodies which have human sequences and are modified, for example, to remove cysteine that may cause a possible decrease in immunogenicity, an increase in affinity, and undesirable folding. This term also includes antibodies generated in non-human cells by recombination, which enable glycosylation that is not specific to human cells. These antibodies can be prepared in various ways.

In the present description, the term "humanized antibody" means a non-human-derived antibody, in which amino acid residues characteristic for a non-human antibody sequence are substituted with residues found in positions corresponding to those of a human antibody. This "humanization" process is considered to reduce the immunogenicity of the obtained antibody in human. It would be understood that a non-human-derived antibody can be humanized using a technique well known in the present technical field. Please refer to, for example, Winter et al., Immunol. Today 14: 43-46 (1993). The target antibody can be prepared by an engineering approach via a recombination DNA technique of substituting CH1, CH2, CH3, a hinge domain, and/or a framework domain with those of the corresponding human sequence. For example, WO92/02190, and U.S. Pat. Nos. 5,530,101, 5,585,089, 5,693,761, 5,693,792, 5,714,350 and 5,777,085 can be referred to. In the present description, the term "humanized antibody" includes a chimeric human antibody and a CDR-grafted antibody, within the definitions thereof.

The sequence of a framework region (FR) in a variable region of the antibody of the present invention is not particularly limited, unless it substantially affects the specific binding ability of the antibody to the corresponding antigen. The FR region of a human antibody is preferably used, but it is also possible to use FR regions of animal species other than humans (e.g. a mouse, a rat, etc.).

In the present description, the term "phage antibody" is used to mean a scFv antibody generated from phage. That is, the phage antibody is an antibody fragment comprising the amino acid sequence of VH and VL. This fragment may comprise an amino acid sequence serving as a tag, as well as amino acids serving as a linker.

In one aspect, the antibody of the present invention comprises a constant region as well as a variable region (e.g. IgG antibody). The sequence of the constant region is not particularly limited. For example, the constant region of a known human antibody can be used. The heavy chain constant region (CH) of a human antibody is not particularly limited, as long as it belongs to a human immunoglobulin (hereinafter referred to as "hIgG"). Those of hIgG class are preferable, and any one of subclasses belonging to hIgG class, such as hIgG1, hIgG2, hIgG3 or hIgG4, may be used. On the other hand, the light chain constant region (CL) is not particularly limited, as long as it belongs to Mg, and those of κ class or λ class can be used. In addition, constant regions of animal species other than humans (e.g. a mouse or a rat) can also be used.

In the present description, the term "modified body" or "modified antibody" is used to mean that the amino acid sequence of the variable region (CDR sequences and/or FR sequences) of a parent antibody comprises a substitution, deletion, addition and/or insertion of one or multiple amino acids. The "parent antibody" means a TfR006 antibody that has a VH comprising the amino acid sequence shown in SEQ ID NO: 43 and a VL comprising the amino acid sequence shown in SEQ ID NO: 46. In the amino acid sequence, one or several (for example, 1 to 8, preferably 1 to 5, more preferably 1 to 3, and particularly preferably 1 or 2) amino acids are deleted, added, substituted and/or inserted. As a method of preparing the amino acid sequence of an antibody having a binding ability to TfR and/or an antitumor activity, which has been well known to a person skilled in the art, a method of introducing a mutation into a protein has been known. For instance, such a skilled person could prepare a mutant antibody functionally equivalent to an antibody having a TfR-binding activity and/or an antitumor activity by appropriately introducing a mutation into the amino acid sequence of the antibody having a TfR-binding activity and/or an antitumor activity according to a site-directed mutagenesis (Hashimoto-Gotoh, T, Mizuno, T, Ogasahara, Y, an DNA kagawa, M. (1995) An oligodeoxyribonucleotide-directed dual amber method for site-directed mutagenesis. Gene 152, 271-275, Zoller, M J, and Smith, M. (1983) Oligonucleotide-directed mutagenesis of DNA fragments cloned into M13 vectors. Methods Enzymol. 100, 468-500, Kramer, W, Drutsa, V, Jansen, H W, Kramer, B, Pflugfelder, M, and Fritz, H J (1984) The gapped duplex DNA approach to oligonucleotide-directed mutation construction. Nucleic Acids Res. 12, 9441-9456, Kramer W, and Fritz H J (1987) Oligonucleotide-directed construction of mutations via gapped duplex DNA Methods. Enzymol. 154, 350-367, Kunkel, T A (1985) Rapid and efficient site-specific mutagenesis without phenotypic selection. Proc Natl Acad Sci USA. 82, 488-492).

In the present description, the phrase "an activity equivalent to the activity of the parent antibody" is used to mean that the human TfR-binding activity and/or antitumor activity of a certain antibody are equivalent to those of the parent antibody thereof. The term "equivalent" does not necessarily mean the same level of activity. The activity may be increased, or the activity may also be decreased, as long as the antibody has the activity. An antibody having a decreased activity may be an antibody having an activity that is, for example, 30% or more, preferably 50% or more, more preferably 80% or more, further preferably 90% or more, and particularly preferably 95% or more of the activity of the original antibody.

The term "binding activity" means the activity of an antibody to recognize an antigen. This antigen may be an intact TfR expressed on a cell membrane, a truncated form, or a soluble form. In addition, the antigen may be either a TfR having a three-dimensional structure or a denatured TfR. Examples of a means for examining the binding activity include flow cytometry (FACS), enzyme-linked immunosorbent assay (ELISA), Western blotting, microfluorescence measuring technique (FMAT), and surface plasmon resonance (Biacore)

The term "antitumor activity" means the activity of inhibiting the growth or survival of tumor cells. The inhibition of the growth or survival of tumor cells may take place either in vitro or in vivo. Examples of the in vitro antitumor activity include an activity of decreasing the number of tumor cells, an activity of inhibiting an increase in the number of tumor cells, an activity of causing cell death to tumor cells, antibody-dependent cellular cytotoxicity (ADCC), and complement-dependent cytotoxicity (CDC). Examples of the in vivo antitumor activity include an activity of decreasing the weight or volume of a tumor, an activity of inhibiting an increase in tumor weight or volume, an activity of promoting a decrease in tumor weight or volume by another drug, and an activity of inhibiting the death of individuals caused by tumor cells.

Examples of an in vivo animal model include: a xenograft model prepared by transplanting a human cancer tissue-derived cultured cell line into an immunodeficient mouse such as a nude mouse; and a syngeneic graft model prepared by transplanting a cultured mouse cancer cell line into a wild-type mouse having a normal immune system.

A xenograft model can be produced by transplanting a human cancer cell line into various sites of immunodeficient mice such as a nude mouse, including the subcutis, intradermal site, abdominal cavity, or vein.

The aforementioned antibody may comprise a substitution, deletion, addition and/or insertion of one or multiple amino acids with respect to the amino acid sequence of a variable region (a CDR sequence and/or an FR sequence), as far as it has a binding activity to TfR or an antitumor activity that is equivalent to the original antibody. As a method for preparing an antibody having a TfR-binding activity and/or an antitumor activity, which comprises a deletion, addition, substitution and/or insertion of one or several amino acids (for example, 1 to 8, preferably 1 to 5, more preferably 1 to 3, and particularly preferably 1 or 2 amino acids), a method of introducing a mutation into a protein has been well known to a person skilled in the art. For instance, such a skilled person could prepare a mutant antibody functionally equivalent to an antibody having a TfR-binding activity and/or an antitumor activity by appropriately introducing a mutation into the amino acid sequence of the antibody having a TfR-binding activity and/or an antitumor activity according to a site-directed mutagenesis (Hashimoto-Gotoh, T, Mizuno, T, Ogasahara, Y, an DNA kagawa, M. (1995) An oligodeoxyribonucleotide-directed dual amber method for site-directed mutagenesis. Gene 152, 271-275, Zoller, M J, and Smith, M. (1983) Oligonucleotide-directed mutagenesis of DNA fragments cloned into M13 vectors. Methods Enzymol. 100, 468-500, Kramer, W, Drutsa, V, Jansen, H W, Kramer, B, Pflugfelder, M, and Fritz, H J (1984) The gapped duplex DNA approach to oligonucleotide-directed mutation construction. Nucleic Acids Res. 12, 9441-9456, Kramer W, and Fritz H J (1987) Oligonucleotide-directed construction of mutations via gapped duplex DNA Methods. Enzymol. 154, 350-367, Kunkel, T A (1985) Rapid and efficient site-specific mutagenesis without phenotypic selection. Proc Natl Acad Sci USA. 82, 488-492), etc.

As such, an antibody, which comprises a mutation of one or several amino acids in a variable region thereof and has a TfR-binding activity and/or an antitumor activity, is also included in the antibody of the present invention.

The antibody of the present invention is not limited by its origin, and it may be an antibody derived from any animal, such as a human antibody, a mouse antibody, or a rat antibody. Also, the present antibody may be a chimeric antibody or a humanized antibody. In a preferred aspect, the antibody of the present invention is a human antibody.

The antibodies of the present invention may be different from one another in terms of amino acid sequence, molecular weight, isoelectric point, the presence or absence of a sugar chain or the form thereof, etc., depending on the after-mentioned cells or hosts that generate the antibodies, or a purification method. As long as the obtained antibody has an activity equivalent to the antibody of the present invention, it is included in the present invention. For example, an antibody that undergoes a modification after it has been translated to the amino acid sequence described in the present description is also included in the present invention. Moreover, an antibody that has undergone a posttranslational modification on a site other than those for the known posttranslational modification is also included in the present invention, as long as it has an activity equivalent to the antibody of the present invention. Furthermore, when the antibody of the present invention is allowed to express in prokaryotic cells such as *Escherichia coli*, a methionine residue is added to the N-terminus of the amino acid sequence of the original antibody. The antibody of the present invention includes such an antibody as well. An antibody that has undergone a posttranslational modification on a site other than those for the known posttranslational modification is also included in the present invention, as long as it has an activity equivalent to the antibody of the present invention.

Production of Antibody (1) Production of scFv Reacting with Antigen Using Phage Display Library The antibody of the present invention can be prepared by several methods known in the present technical field. For example, using a phage display technique, a library comprising a repertoire of antibodies having various affinity for TfR can be provided. Subsequently, such a library can be screened to identify and isolate antibodies against TfR. Preferably, the phage library is a scFv phage display library that is generated using human VL and VH cDNA that has been prepared from mRNA isolated from human B cells. A method of preparing and screening such a library is known in the present technical field. A genetic substance is recovered from phage clones exhibiting reactivity that have been screened using a human TfR as an antigen. By analyzing the selected phage gene, the DNA sequences of VH and VL encoding the variable region of a human antibody binding to the antigen can be determined. Using this scFv sequence, IgG is prepared from scFv, so as to obtain a human antibody.

(2) Preparation of IgG from scFv (Preparation of Human Antibody)

An H chain or L chain expression vector is constructed, and it is then allowed to express in a host cell. Thereafter, the supernatant containing secreted protein is recovered and is then purified, so as to obtain a human antibody. Alternatively, such a human antibody can also be obtained by allowing VH and VL to express in a single vector (tandem type). These methods are well known, and can be carried out with reference to WO92/01047, WO92/20791, WO93/06213, WO93/11236, WO93/19172, WO95/01438, WO95/15388, WO97/10354, etc.

Specifically, DNA encoding VH is ligated to another DNA molecule encoding a heavy chain constant region (CH1, CH2 and CH3), so as to obtain a full-length heavy chain gene. The sequence of a human heavy chain constant region gene is known in the present technical field (for example, Kabat, E. A. et al., (1991) Sequences of Proteins of Immunological Interest, 5$^{th}$ edition, U. S. Department of Health and Human Services, NIH Publication No. 91-3242), and a DNA fragment including such a region can be obtained by standard PCR amplification. The heavy chain constant region may be the constant region of IgG1, IgG2, IgG3, IgG4, IgA, IgE, IgM or IgD. The most preferred constant region is that of IgG1 or IgG2. The constant region sequence of IgG1 may include any given various alleles or allotypes known to be generated among different individuals, such as Gm (1), Gm (2), Gm (3) or Gm (17). These allotypes correspond to a substitution of amino acids naturally-occurring in the constant region of IgG1.

DNA encoding VL is ligated to another DNA molecule encoding the light chain constant region CL, so as to obtain a full-length L chain gene (and a Fab light chain gene). The sequence of a human light chain constant region gene is known in the present technical field (for example, Kabat, E. A. et al., (1991) Sequences of Proteins of Immunological Interest, 5$^{th}$ edition, U. S. Department of Health and Human Services, NIH Publication No. 91-3242), and a DNA fragment including such a region can be obtained by standard PCR amplification. The light chain constant region may be the constant region of κ or λ. The κ constant region may include any given various alleles known to be generated among different individuals, such as Inv (1), Inv (2) or Inv (3). The λ constant region may be derived from any one of the three λ, genes.

The thus obtained DNA encoding an H chain or L chain is inserted into a vector to construct an expression vector, and the constructed expression vector is then allowed to express in a host cell. Thereafter, the supernatant containing secreted protein is recovered and purified to obtain a human antibody. Examples of the expression vector include a plasmid, retrovirus, adenovirus, adeno-associated virus (AAV), plant viruses such as cauliflower mosaic virus or tobacco mosaic virus, a cosmid, YAC, and EBV-derived episome. An expression vector and an expression regulatory sequence are selected, so that they are suitable for a host cell used for expression. An antibody light chain gene and an antibody heavy chain gene can be inserted into different vectors, or the two genes can also be inserted into a single expression vector. An antibody gene is inserted into an expression vector by a standard method (for example, ligation of a complementary restriction site on an antibody gene fragment to a vector, or blunt-ended ligation applied when no restriction sites are present).

A favorable vector encodes a functionally completed human CH or CL immunoglobulin sequence having a suitable restriction site, which has been constructed by an engineering approach such that any given VH or VL sequence can be easily inserted and then expressed as described above. In such a vector, splicing generally takes place between a splice donor site in the inserted J region and a splice acceptor site preceding a human C domain, or such splicing also takes place in a splice region existing in a human CH exon. Polyadenylation and transcription termination take place in a natural chromosomal site downstream of a coding region. A recombinant expression vector can also encode a signal peptide that promotes the secretion of an antibody chain derived from a host cell. An antibody chain gene can be cloned into a vector, such that a signal peptide can be ligated in-frame to the amino terminus of an immunoglobulin chain. The signal peptide may be either an immunoglobulin signal peptide or a heterogeneous signal peptide (namely, it may be a non-immunoglobulin protein-derived signal peptide).

An expression vector used for the antibody of the present invention may also have sequences such as a sequence for regulating replication of the vector in a host cell (e.g. a replication origin) or a selective marker gene sequence, as well as an antibody gene and a regulatory sequence. The selective marker gene promotes selection of a host cell into which a vector has been introduced. For instance, the selective marker generally imparts resistance to drugs such as G418, hygromycin or methotrexate to a host cell into which the vector has been introduced. Preferred selective marker genes include a dihydrofolate reductase (DHFR) gene (used in selection/amplification by methotrexate as a dhfr-host cell), a neomycin phosphotransferase gene (used in selection by G418), and a glutamate synthase gene.

A host cell is transformed with an antibody gene expression vector constructed by the above-described method. Any type of cell may be used as a host cell, as long as it can generate the antibody of the present invention. Examples of such a host cell include bacteria, yeast, animal cells, insect cells, and plant cells. Among these cells, animal cells are preferable. Examples of the animal cells include Chinese hamster ovary cells CHO/dhfr(−) and CHO/DG44, monkey-derived cells COS (A. Wright & S. L. Morrison, J. Immunol. 160, 3393-3402 (1998)), and SP2/O cells (mouse myeloma) (K. Motmans et al., Eur. J. Cancer Prev. 5, 512-5199 (1996), R. P. Junghans et al., Cancer Res. 50, 1495-1502 (1990)). For transformation, a lipofectin method (R. W. Malone et al., Proc. Natl. Acad. Sci. USA 86, 6007 (1989), P. L. Felgner et al., Proc. Natl. Acad. Sci. USA 84, 7413 (1987)), an electroporation method, a calcium phosphate method (F. L. Graham & A. J. van der Eb, Virology 52,456-467 (1973)), a DEAE-Dextran method, and the like are preferably applied.

A transformant is cultured, and a human antibody is then separated from the cells of the transformant or a culture medium thereof. For separation/purification of the antibody, methods such as centrifugation, ammonium sulfate fractionation, salting-out, ultrafiltration, affinity chromatography, ion exchange chromatography and gel filtration chromatography can be used by appropriately combining them.

Antibody Fragments

An antibody fragment can be prepared based on the antibody of the present invention, or based on the sequence information of a gene encoding the antibody of the present invention. Examples of the antibody fragment include Fab, Fab', F(ab')$_2$, scFv, and dsFv antibodies.

Fab is obtained by digesting IgG by papain in the presence of cysteine. It is an antibody fragment with a molecular weight of approximately 50,000, which is constituted with L chain and H chain variable regions, and an H chain fragment consisting of a CH1 domain and a portion of a hinge region. In the present invention, Fab can be obtained by digesting the above-described antibody by papain. In addition, Fab can also be prepared by incorporating DNA encoding a portion of the H chain and the L chain of the above-described antibody into a suitable vector, then performing transformation with the resulting vector, and then obtaining Fab from the transformant.

Fab' is an antibody fragment with a molecular weight of approximately 50,000, which is obtained by cleaving a disulfide bond between the H chains of the below-mentioned F(ab')$_2$. In the present invention, Fab' can be obtained by digesting the above-described antibody by pepsin, and then cleaving a disulfide bond with a reducing agent. In addition, as with Fab, Fab' can also be prepared by genetic engineering using DNA encoding the Fab'.

F(ab')$_2$ is an antibody fragment with a molecular weight of approximately 100,000 which is obtained by digesting IgG by pepsin, wherein one fragment (Fab') constituted with L chain and H chain variable regions and an H chain fragment consisting of a CH1 domain and a portion of a hinge region is linked to the other fragment (Fab') via a disulfide bond. In the present invention, F(ab')$_2$ can be obtained by digesting the above-described antibody by pepsin. In addition, as with Fab, F(ab')$_2$ can also be prepared by genetic engineering using DNA encoding the F(ab')$_2$.

scFv is an antibody fragment obtained by ligating the C-terminus of one chain of Fv consisting of an H chain variable region and an L chain variable region to the N-terminus of the other chain thereof, using a suitable peptide linker, so as to form a single chain. (GGGGS)$_3$ having high flexibility can be used, for example, as such a peptide linker. For instance, DNA encoding the H chain variable region and L chain variable region of the above-described antibody and DNA encoding a peptide linker are used to construct DNA encoding a scFv antibody, and the thus constructed DNA is then incorporated into a suitable vector. Thereafter, scFv can be prepared from a transformant obtained by transformation with the aforementioned vector.

dsFv is a Fv fragment obtained by introducing a Cys residue into a suitable site in each of an H chain variable region and an L chain variable region, and then stabilizing the H chain variable region and the L chain variable region by a disulfide bond. The site in each chain, into which the Cys residue is to be introduced, can be determined based on a conformation predicted by molecular modeling. In the present invention, for example, a conformation is predicted from the amino acid sequences of the H chain variable region and L chain variable region of the above-described antibody, and DNA encoding each of the H chain variable region and the L chain variable region, into which a mutation has been introduced based on such prediction, is then constructed. The thus constructed DNA is incorporated into a suitable vector. Thereafter, dsFv can be then prepared from a transformant obtained by transformation with the aforementioned vector.

Further, it is also possible to ligate the scFv antibody, the dcFv antibody or the like using a suitable linker, or to fuse such an antibody fragment with streptavidin, so as to multimerize the antibody fragment.

Pharmaceutical Composition

According to the present invention, a pharmaceutical composition comprising the antibody of the present invention is provided. In one embodiment, the present invention relates to the treatment of cancer, but is not limited thereto. Diseases caused by high expression of TfR, other than cancer, are also included in the scope of the present invention. In a more preferred embodiment, examples of the cancer include: solid cancer (e.g. lung cancer, colon cancer, stomach cancer, bladder cancer, pancreatic cancer, prostate cancer, hepatic cancer, cervical cancer, uterine cancer, ovarian cancer, breast cancer, head and neck cancer, skin cancer, etc.); and blood cancer (e.g. leukemia, lymphoma, myeloma, etc.). In another preferred embodiment of the present invention, the cancer is adult T-cell leukemia (ATL).

In one aspect of the pharmaceutical composition of the present invention, the antibody of the present invention is used as an active ingredient. The cell growth-inhibiting activity, cell death-inducing activity, ADCC activity, CDC activity and the like of the antibody are utilized, and thereby, the antitumor effects of the antibody are exhibited. The antibody may have only one of the aforementioned activities, or may simultaneously have a plurality of the aforementioned activities. That is, a naked antibody is used as an active ingredient of the pharmaceutical composition.

In another aspect, the antibody of the present invention can be used as a cancer therapeutic agent in a missile therapy that specifically targets cancer tissues. Specifically, the missile therapy is a treatment method, which comprises administering to cancer cells, an antibody to which a substance causing damage to the cancer cells has been bound, and allowing the substance to specifically transfer to the cancerous portion, so as to address the achievement of therapeutic effects and reduction in side effects.

The substances causing damage to cancer cells are cytotoxic substances such as a drug, a toxin or a radioactive substance. The binding of such a cytotoxic substance to the antibody can be carried out by a method known to a person skilled in the art (Clin Cancer Res. 2004 Jul. 1; 10(13): 4538-49).

As a drug to be bound to the antibody, a known substance causing damage to cancer cells can be used. Examples of such a drug include duocarmycin, an analog and a derivative of duocarmycin, CC-1065, a duocarmycin analog comprising CBI as a main ingredient, a duocarmycin analog comprising MCBI as a main ingredient, a duocarmycin analog comprising CCBI as a main ingredient, doxorubicin, a doxorubicin conjugate, morpholino-doxorubicin, cyanomorpholino-doxorubicin, dolastatin, dolestatin-10, combretastatin, calicheamicin, maytansine, a maytansine analog, DM1, DM2, DM3, DM4, DMI, auristatin E, auristatin EB (AEB), auristatin EFP (AEFP), monomethyl auristatin E (MMAE), monomethyl auristatin F (MMAF), 5-benzoyl valeric acid-AB ester (AEVB), tubulysin, disorazole, epothilone, paclitaxel, docetaxel, SN-38, topotecan, rhizoxin, echinomycin, colchicine, vinblastine, vindesine, estramustine, cemadotin, eleutherobin, methotrexate, methopterin, dichloromethotrexate, 5-fluorouracil, 6-mercaptopurine, cytosine arabinoside, melphalan, leurosine, leurosideine, actinomycin, daunorubicin, a daunorubicin conjugate, mitomycin C, mitomycin A, carminomycin, aminopterin, talisomycin, podophyllotoxin, a podophyllotoxin derivative, etoposide, etoposide phosphate, vincristine, taxol, taxotere retinoic acid, butyric acid, $N^8$-acetyl spermidine and camptothecin, but examples are not limited thereto.

The antibody may be directly bound to a drug via a linking group possessed thereby or the like, or they may be indirectly bound to each other via a linker or another substance.

Examples of the use of a linking group in the direct binding of a drug include a disulfide bond using an SH group and a bond mediated by maleimide. For example, an intramolecular disulfide bond in the Fc region of the antibody and a disulfide bond of the drug are reduced, and they are then bound to each other via a disulfide bond. There is also a method involving mediation of maleimide. In addition, an alternative method is a method of introducing cysteine into the antibody by genetic engineering.

It is also possible to indirectly bind the antibody to the drug via another substance (linker). The linker desirably has one or two or more types of functional groups reacting with the antibody or the drug, or with both of them. Examples of such a functional group include an amino group, a carboxyl group, a mercapto group, a maleimide group, and a pyridinyl group.

Examples of the linker used herein include N-succinimidyl 4-(maleimidomethyl)cyclohexanecarboxylate (SMCC), N-succinimidyl 4-(N-maleimidomethyl)-cyclohexan-1-carboxy-(6-amidocaproate) (LC-SMCC), κ-maleimidoundecanoic acid N-succinimidyl ester (KMUA), γ-maleimidobutyric acid N-succinimidyl ester (GMBS), ε-maleimidocaproic acid N-hydroxysuccinimide ester (EMCS), m-maleimidobenzoyl-N-hydroxysuccinimide ester (MBS), N-(α-maleimidoacetoxy)-succinimide ester (AMAS), succinimidyl 6-(β-maleimidopropionamido) hexanoate (SMPH), N-succinimidyl 4-(p-maleimidophenyl) butylate (SMPB), N-(p-maleimidophenyl)isocyanate (PMPI), 6-maleimidocaproyl (MC), maleimidopropanoyl (MP), p-aminobenzyloxycarbonyl (PAB), N-succinimidyl 4-(2-pyridylthio)pentanoate (SPP) and N-succinimidyl(4-iodo-acetyl)aminobenzoate (SIAB), but examples are not limited thereto. Moreover, the linker may be a peptide linker such as valine-citrulline (Val-Cit) or alanine-phenylalanine (ala-phe), or the above-listed linkers may be appropriately combined and may be used.

With regard to a method of binding a drug to an antibody, such a drug can be bound to an antibody according to the methods described, for example, in Cancer Research; 68(22) 9280 (2008), Nature Biotechnology; 26(8) 925 (2008), Bio Conjugate Chemistry; 19, 1673 (2008), Cancer Research; 68(15) 6300 (2008), JP Patent Publication (Kohyo) No. 2008-516896 A, etc.

The toxin may be what is called immunotoxin, in which a toxin is allowed to bind to the antibody in a chemical or genetically engineering manner. Examples of the toxin include diphtheria toxin A chain, *Pseudomonas* endotoxin, ricin chain, no sugar chain ricin A chain, gelonin, and saporin.

As a radioactive substance used herein, a radioactive substance known to a person skilled in the art can be used. Examples of such a radioactive substance include yttrium 90 ($^{90}$Y), rhenium 186 ($^{186}$Re), rhenium 188 ($^{188}$Re), copper 67 ($^{67}$Cu), iron 59 ($^{59}$Fe), strontium 89 ($^{89}$Sr), gold 198 ($^{198}$Au), mercury 203 ($^{203}$Hg), lead 212 ($^{212}$Pb), dysprosium 165 ($^{165}$Dy), ruthenium 103 ($^{103}$Ru), bismuth 212 ($^{212}$Bi), bismuth 213 ($^{213}$Bi), holmium 166 ($^{166}$Ho), samarium 153 ($^{153}$Sm), and lutetium 177 ($^{177}$Lu). Preferred radioactive substances are $^{90}$Y, $^{153}$Sm, and $^{177}$Lu.

The binding of such a radioactive substance to the antibody can be carried out by a method known to a person skilled in the art (Bioconjug Chem. 1994 Mar.-Apr.; 5(2): 101-4.).

Cancer therapy, which uses an antibody to which a compound containing a radioisotope is bound, can be carried out by a method known to a person skilled in the art (Bioconjug Chem. 1998 Nov.-Dec.; 9(6): 773-82.). Specifically, at first, an antibody to which a radioisotope-containing compound has been bound is administered in a small amount to a patient, and scintigraphy is then performed on the entire body of the patient. It is confirmed that the binding level of cells in normal tissues to the antibody is low, and that the binding level of cancer cells to the antibody is high. Thereafter, the antibody to which the radioisotope-containing compound has been bound is administered in a large amount to the patient.

A preparation, which comprises a pharmaceutical composition containing the anti-human TfR antibody of the present invention, is also included in the scope of the present invention. Such a preparation preferably comprises a physiologically acceptable diluent or carrier, as well as the pharmaceutical composition containing the antibody. The preparation may also be a mixture with another antibody, or with another drug such as an anticancer agent. Examples of a suitable carrier used herein include a normal saline, a phosphate buffered saline, a phosphate buffered saline with glucose, and a buffered saline, but examples are not limited thereto. Otherwise, the antibody is freeze-dried, and when needed, the aforementioned buffered aqueous solution may be added thereto to reconstitute the antibody, and the thus reconstituted antibody may be then used Examples of the dosage form of the preparation include: oral administration, which uses a tablet, a capsule, a granule, a powder agent, a syrup, etc.; and parenteral administration, which includes injections (subcutaneous injection, intravenous injection, intramuscular injection, intraperitoneal injection, etc.), per-cutaneous administration, transmucosal administration, transnasal administration, transpulmonary administration, the use of a suppository, etc. The preparation comprising the pharmaceutical composition of the present invention may be administered alone, or it may also be used in combination with other drugs.

The applied dose of the pharmaceutical composition of the present invention is different depending on symptom, age, body weight, etc. In general, in the case of oral administration, the present pharmaceutical composition is administered at an amount of approximately 0.01 mg to 1,000 mg per day per adult, in terms of the amount of an antibody contained therein. Such dose can be administered once or divided over several administrations per day. On the other hand, in the case of parenteral administration, the present pharmaceutical composition can be administered at an amount of approximately 0.01 mg to 1,000 mg for a single administration via subcutaneous injection, intramuscular injection or intravenous administration.

The present invention will be described more in detail in the following examples. However, these examples are not intended to limit the scope of the present invention.

EXAMPLES

Example 1

Screening for Phage Antibody Using Cancer Cell Line (1) Screening for Phage Antibody Bound to Cancer Cells (Hepatic Cancer Cell Line HepG2)

HepG2 cells were cultured in 15-cm dish, and then, using 2 mg/mL collagenase I/cell dissociation buffer (Gibco BRL), the cultured cells were then removed from the dish. The cells were recovered and were then washed with cooled PBS. Thereafter, a human antibody phage library ($1 \times 10^{13}$ cfu) was mixed with the resulting cells, and a reaction solution (1% BSA, 0.1% NaN3, and MEM) was then added thereto to a final volume of 1.6 mL. The obtained mixture was slowly rotated at 4° C. for 4 hours for performing a reaction. After completion of the reaction, the reaction solution was divided into two aliquots, and 0.6 mL of an organic solution (dibutyl phthalate and cycloheximide (9:1)) that had previously been prepared was layered on each aliquot, and the thus obtained mixture was then centrifuged (300 rpm) for 2 minutes using a microcentrifuge. Thereafter, the supernatant was discarded, and cells precipitated at the bottom of the tube were suspended in 0.7 mL of 1% BSA/MEM. Then, 0.7 mL of an organic solvent was further layered on the suspension. Centrifugation was carried out in the same manner as described above, the supernatant was then discarded, and the cells were then suspended in 0.3 mL of PBS, followed by freezing with liquid nitrogen (Patent Literature 19, WO 2008/007648).

The frozen cells were thawed at 37° C., and were then infected with 20 mL of *Escherichia coli* DH12S (OD0.5) for 1 hour. The phage-infected *Escherichia coli* was placed in 600 mL of a 2×YTGA medium (2×YT, 200 µg/mL ampicisulfate, and 1% glucose), and it was then cultured at 30° C. overnight. Thereafter, 10 mL of the culture was placed in 200 mL of a 2×YTA medium (2×YT and 200 µg/mL ampicisulfate), and it was then cultured at 37° C. for 1.5 hours. Then, $1 \times 10^{11}$ helper phage KO7 was added to the culture, and the obtained mixture was further cultured at 37° C. for 1 hour. Subsequently, 800 mL of a 2×YTGAK medium (2×YT, 200 µg/mL ampicisulfate, 0.05% glucose, and 50 µg/mL kanamycin) was added to the culture, and the obtained mixture was then cultured at 30° C. overnight. Thereafter, the supernatant was recovered by centrifugation (8000 rpm) for 10 minutes. To the recovered supernatant, 200 mL of a PEG solution (20% polyethylene glycol 6000 and 2.5M NaCl) was added, and the obtained mixture was fully stirred. Thereafter, the reaction mixture was subjected to centrifugation (8000 rpm) for 10 minutes to precipitate phages. The phages were suspended in 10 mL of PBS. The obtained solution was defined as phages obtained from the $1^{st}$ screening.

Subsequently, the $2^{nd}$ screening was carried out. The cultured cells ($2 \times 10^7$) were mixed with the phages from the $1^{st}$ screening ($1 \times 10^{10}$), and a reaction solution (1% BSA, 0.1% NaN3, and MEM) was added to the mixture to a final volume of 0.8 mL. Thereafter, the same operations as those in the aforementioned $1^{st}$ screening were carried out, so as to obtain phages from the $2^{nd}$ screening.

The $3^{rd}$ screening was carried out using the phages ($1 \times 10^9$) obtained from the $2^{nd}$ screening in the same manner as described above.

(2) Analysis of Phage Antibodies

The phages obtained from the $3^{rd}$ screening were recovered, and the DNA sequences thereof were then analyzed by the existing method. Incomplete antibodies comprising deletions in the regions or antibodies having overlapping sequences were removed, so that phage antibodies each having an independent antibody sequence could be obtained (see Japanese Patent No. 4870348).

By the same method, phage antibodies reacting with cancer antigens were screened using 21 types of cancer cells shown in the following Table 1. As a result, 1863 phage antibodies each having an independent sequence were obtained, as shown in Table 1.

TABLE 1

| Cancer cells | Number of obtained phages |
| --- | --- |
| CO-2 | 102 |
| MKN45 | 90 |
| OCTH-16 | 82 |
| HepG2 | 410 |
| NCI-H441 | 80 |
| K562 | 33 |
| U937 | 107 |
| HL-60 | 107 |
| MV4-11 | 46 |
| KF28 | 62 |
| NCI-N87 | 50 |
| RERF-LC-AI | 73 |
| SW480 | 46 |
| MCF7 | 73 |
| LNCap.FGC | 60 |
| MDA-MB-231 | 78 |
| U-87MG | 62 |
| T98G | 71 |
| DU-145 | 96 |
| MMAc | 76 |
| G-361 | 59 |

Example 2

Screening for Phages Reacting with Soluble Human TfR (1) Production of Soluble TfR Antigen-Generating Cells Using cancer cell lines MIAPaCa2 and SKOV-3, the cDNA of TfR was prepared by a PCR method. The cDNA of a TfR extracellular domain was prepared by an ordinary method, and the prepared cDNA was then inserted into pCMV-Script (manufactured by Clontech) to construct a soluble TfR antigen expression vector. This expression vector was introduced into a cell line 293T, so as to prepare cells which generate a soluble TfR antigen.

(2) Screening for Positive Phages by ELISA

A supernatant of the above-described soluble TfR-generating cells was recovered, and it was then purified to obtain a soluble TfR antigen. Using this soluble TfR antigen, the reactivity of antigen-antibody was examined by ELISA. Specifically, the concentration of the soluble TfR antigen was adjusted to be 10 μg/mL with PBS, and it was then added to Immuno Module/Strip Plates (NUNK) in an amount of 50 μL/well. It was left at rest at 37° C. for 2 hours. Thereafter, the soluble TfR antigen was discarded, and a blocking solution (5% skimmed milk/0.05% NaN3/PBS) was added thereto in an amount of 200 μL/well, followed by performing blocking at 37° C. for 2 hours. Thereafter, the blocking solution was removed, and the plate was then washed with PBS. The culture supernatant of the above-mentioned phage (Table 1) was added to each well in an amount of 100 μL/well, and it was then reacted at 37° C. for 1 hour. The resultant was washed with PBS five times, and 1 μg/mL Rabbit anti-cp3 that had been diluted with PBS/0.05% Tween 20 was then added to the resultant in an amount of 100 μL/well. The thus obtained mixture was reacted at 37° C. for 1 hour. The resultant was washed with PBS five times, and anti-Rabbit IgG (H+L)-HRP that had been 2000 times diluted with PBS/0.05% Tween 20 was further added to the resultant in an amount of 100 μL/well. The thus obtained mixture was reacted at 37° C. for 1 hour. The resultant was washed with PBS five times, and OPD in a 0.1 M citrate phosphate buffer (pH 5.1)+0.01% $H_2O_2$ was then added thereto in an amount of 100 μL/well. The obtained mixture was reacted at room temperature for 5 minutes. Thereafter, $2NH_2SO_2$ was added to the reaction solution in an amount of 100 μL/well, so as to terminate the coloring reaction. Subsequently, the absorbance at 492 nm was measured using SPECTRA max340PC (Molecular Devices). As a result, twenty strains of phages exhibiting a significant positive reaction to the soluble TfR antigen were found in the 1863 strains of phages. The DNA sequences of these 20 strains of phages were analyzed, and as a result, it was confirmed that all of their CDR sequences were novel. Among these CDR sequences, the CDR sequences of the TfR006 antibody are as follows.

```
TfR006
VH CDR1: SEQ ID NO: 1,

VH CDR2: SEQ ID NO: 2,

VH CDR3: SEQ ID NO: 3

VL CDR1: SEQ ID NO: 4,

VL CDR2: SEQ ID NO: 5,

VL CDR3: SEQ ID NO: 6

SEQ ID NO: 1: SYGMH

SEQ ID NO: 2: VISFDGSSKYYADSVKG

SEQ ID NO: 3: DSNFWSGYYSPVDV

SEQ ID NO: 4: TRSSGSIASNSVQ

SEQ ID NO: 5: YEDTQRPS

SEQ ID NO: 6: QSYDSAYHWV
```

Example 3

VH Modification of TfR006 Antibody (1) Substitution of One Amino Acid in VH CDR3 Sequence of TfR006 Antibody Kabat Nos. 96, 97, 98, and 100 of the CDR3 (SEQ ID NO: 3) of the VH (SEQ ID NO: 43) of a TfR006 antibody were each substituted with other amino acids. The TfR006 antibody was mutated, such that the amino acid of Kabat No. 96 in the VH of a modified TfR402 antibody was changed from S to G (SEQ ID NO: 7), the amino acid of Kabat No. 97 in the VH of a TfR403 antibody was changed from N to A (SEQ ID NO: 8), the amino acid of Kabat No. 98 in the VH of a TfR404 antibody was changed from F to L (SEQ ID NO: 9), and the amino acid of Kabat No. 100 in the VH of a TfR406 antibody was changed from S to G (SEQ ID NO: 10). The sequences after the substitutions are shown in Table 2. In addition, Q of Kabat No. 1 in all the modified bodies was substituted with D, so that the N-terminal pyroglutamic acid could not be formed.

TABLE 2

Table 2: CDR3 sequences of modified antibodies

| Kabat No. | . . . 100<br>. . . 102<br>567890abcdef12 | |
|---|---|---|
| TfR006 HV CDR3 | DSNFWSGYYSPVDV | SEQ ID NO: 3 |
| TfR402 HV CDR3 | DGNFWSGYYSPVDV | SEQ ID NO: 7 |
| TfR403 HV CDR3 | DSAFWSGYYSPVDV | SEQ ID NO: 8 |
| TfR404 HV CDR3 | DSNLWSGYYSPVDV | SEQ ID NO: 9 |
| TfR406 HV CDR3 | DSNFWGGYYSPVDV | SEQ ID NO: 10 |

(2) Substitution of 3 Amino Acids in VH CDR3 Sequence of TfR006 Antibody

Three amino acids in the VH CDR3 sequence of a TfR006 antibody were substituted with other amino acids to prepare a modified antibody. Three out of six amino acids ranging from Kabat Nos. 95 to 100 in the CDR3 were substituted with other amino acids. The VH of a TfR407 antibody was mutated such that it involved Kabat Nos. N97A (wherein the 97th amino acid N was substituted with A), F98L and S100G (SEQ 11) NO: 11), the HV of a TfR408 antibody was mutated such that it involved Kabat Nos. S96G, F98L and S100G (SEQ ID NO: 12), the HV of a TfR409 antibody was mutated such that it involved Kabat Nos. S09G; N97A and S100G (SEQ ID NO: 13), and a TfR410 was mutated such that it involved Kabat Nos. S96G, N97A and F98L (SEQ ID NO: 14) (Table 3). In addition, Q of Kabat No. 1 in all the modified bodies was substituted with D, so that the N-terminal pyroglutamic acid could not be formed.

TABLE 3

Table 3: CDR3 sequences of modified antibodies

| Kabat No. | . . . 100<br>. . . 102<br>567890abcdef12 | |
|---|---|---|
| TfR006 HV CDR3 | DSNFWSGYYSPVDV | SEQ ID NO: 3 |
| TfR407 HV CDR3 | DSALWGGYYSPVDV | SEQ ID NO: 11 |

TABLE 3-continued Table 3: CDR3 sequences of modified antibodies

| Kabat No. | . . . 100<br>. . . 102<br>567890abcdef12 | |
|---|---|---|
| TfR408 HV CDR3 | DGNLWGGYYSPVDV | SEQ ID NO: 12 |
| TfR409 HV CDR3 | DGAFWGGYYSPVDV | SEQ ID NO: 13 |
| TfR410 HV CDR3 | DGALWSGYYSPVDV | SEQ ID NO: 14 |

(3) Substitution of 4 Amino Acids in VH CDR3 Sequence of TfR006 Antibody

Four amino acids in the VH CDR3 sequence of a TfR006 antibody were substituted with other amino acids to prepare a modified TfR411 antibody. Four out of six amino acids ranging from Kabat Nos. 95 to 100 in the CDR3 were mutated such that they involved Kabat Nos. S96G, N97A, F98L, and S100G (SEQ ID NO: 15) (Table 4). In addition, Q of Kabat No. 1 in this modified body was substituted with D, so that the N-terminal pyroglutamic acid could not be formed.

TABLE 4

Table 4: CDR3 sequence of modified antibody

| Kabat No. | . . . 100<br>. . . 102<br>567890abcdef12 | |
|---|---|---|
| TfR006 HV CDR3 | DSNFWSGYYSPVDV | SEQ ID NO: 3 |
| TfR411 HV CDR3 | DGALWGGYYSPVDV | SEQ ID NO: 15 |

(4) Amino Acid Substitution in VH CDR2 Sequence of TfR006 Antibody

Amino acids in the VH CDR2 sequence of a TfR006 antibody were substituted with other amino acids to prepare modified antibodies. The performed modifications are shown in the following table.

TABLE 5

Table 5: CDR2 sequences of modified antibodies

| Kabat No. | 50 . . . 65<br>012a3456789012345 | |
|---|---|---|
| TfR006 HV CDR2 | VISFDGSSKYYADSVKG | SEQ ID NO: 2 |
| TfR434 HV CDR2 | VISYDGSSKYYADSVKG | SEQ ID NO: 52 |
| TfR435 HV CDR2 | VISFDGSNKYYADSVKG | SEQ ID NO: 53 |
| TfR436 HV CDR2 | VISYDGSNKYYADSVKG | SEQ ID NO: 54 |

(5) Other VH Modifications of TfR006 Antibody

A germline gene that is closest to the amino acid sequence of the VH of a TfR006 antibody was examined by searching the IMGT database. As a result, the closest germline gene was found to be IGHV3-30. FIG. 3 shows an alignment of the VH amino acid sequence (SEQ ID NO: 43) of a TfR006 antibody, the amino acid sequence (SEQ ID NO: 44) of IGHV3-30, and the consensus amino acid sequence (SEQ ID NO: 45) of human germline gene subgroup III. TfR006 VH mutants each having different amino acid combinations that ranged from TfR412VH (SEQ ID NO: 16) to TfR420HV (SEQ ID NO: 24) were prepared.

SEQ ID NO: 16: TfR412 VH
DVQLVESGGGLVQPGGSLRLSCAASGFPFKSYGMQWVRQAPGKGLEWVAV

ISFDGSSRYYADSVKGRFTISRDNSKNTLYLQMNSLRAEDTAVYYCARDG

ALWGGYYSPVDVWGQGTLVTVS

SEQ ID NO: 17: TfR413 VH
DVQLVESGGGLVQPGGSLRLSCAASGFPFKSYAMHWVRQAPGKGLEWVAV

ISYDGSNKYYADSVKGRFTISRDNSKNTLYLQMNSLRAEDTAVYYCARDG

ALWGGYYSPVDVWGQGTLVTVSS

SEQ ID NO: 18: TfR414 VH
DVQLVESGGGLVQPGGSLRLSCAASGFPFKSYAMHWVRQAPGKGLEWVAV

ISFDGSNKYYADSVKGRFTISRDNSKNTLYLQMNSLRAEDTAVYYCARDG

ALWGGYYSPVDVWGQGTLVTVSS

SEQ ID NO: 19: TfR415 VH
DVQLVESGGGLVQPGGSLRLSCAASGFPFKSYAMHWVRQAPGKGLEWVAV

ISFDGGSRYYADSVKGRFTISRDNSKNTLYLQMNSLRAEDTAVYYCARDG

ALWGGYYSPVDVWGQGTLVTVSS

SEQ ID NO: 20: TfR416 VH
DVQLVESGGGLVQPGGSLRLSCAASGFPFKSYGMQWVRQAPGKGLEWVAV

ISFDGGSRYYADSVKGRFTISRDNSKNTLYLQMNSLRAEDTAVYYCARDG

ALWGGYYSPVDVWGQGTLVTVSS

SEQ ID NO: 21: TfR417 VH
DVQLVESGGGLVQPGGSLRLSCAASGFTFSSYAMQWVRQAPGKGLEWVAV

ISFDGGSRYYADSVKGRFTISRDNSKNTLYLQMNSLRAEDTAVYYCARDG

ALWGGYYSPVDVWGQGTLVTVSS

SEQ ID NO: 22: TfR418 VH
DVQLVESGGGLVQPGGSLRLSCAASGFTFSSYGMQWVRQAPGKGLEWVAV

ISFDGGSRYYADSVKGRFTISRDNSKNTLYLQMNSLRAEDTAVYYCARDG

ALWGGYYSPVDVWGQGTLVTVSS

SEQ ID NO: 23: TfR419 VH
DVQLVESGGGLVQPGGSLRLSCAASGFTFSSYAMQWVRQAPGKGLEWVSV

ISFDGGNRYYADSVKGRFTISRDNSKNTLYLQMNSLRAEDTAVYYCARDG

ALWGGYYSPVDVWGQGTLVTVSS

SEQ ID NO: 24: TfR420 VH
DVQLVESGGGLVQPGGSLRLSCAASGFTFSSYAMQWVRQAPGKGLEWVSI

VSFDGGNRYYADSIKGRFTISRDNSKNTLYLQMNSLRAEDTAVYYCARDG

ALWGGYYSPIDVWGQGTLVTVSS

SEQ ID NO: 43: TfR006 VH
QVQLVQSGGGVVQPGRSLRLSCAASGFPFKSYGMUWVRQAPGKGLEWVAV

ISFDGSSKYYADSVKGRFTISRDNSKNTLYLQMNSLRGEDTAVYYCARDS

NFWSGYYSPVDVWGQGTTVTVSS

SEQ ID NO: 44: IGHV3-30
QVQLVESGGGVVQPGRSLRLSCAASGFTFSSYGMHWVRQAPGKGLEWVAV

ISYDGSNKYYADSVKGRFTISRDNSKNTLYLQMNSLRAEDTAVYYCAR

SEQ ID NO: 45: Human VH3 consensus
EVQLVESGGGLVQPGGSLRLSCAASGFTFSSYAMSWVRQAPGKGLEWVSV

ISGDGGSTYYADSVKGRFTISRDNSKNTLYLQMNSLRAEDTAVYYCAR

Example 4

VL Modification of TfR006 Antibody (1) VL Modification of TfR006 Antibody

A germline gene that was estimated to be used in TfR006 VL (SEQ ID NO: 46) was searched on the IMGT database. As a result, it was found to be IGLV6-57 (Accession No.: Z73673, SEQ ID NO: 47) (Table 6). Amino acid substitution was found at 5 sites in the VL gene portion, and based on this, VL modified bodies of the TfR006 antibody, TfR421 and TfR422 (TfR421: SEQ ID NO: 25, and TfR422: SEQ ID NO: 26), were prepared. In addition, Q of Kabat No. 1 in such a modified body was substituted with D, so that the N-terminal pyroglutamic acid could not be formed.

TABLE 6

| TfR006 germline gene | | | |
| --- | --- | --- | --- |
| VH | IGHV3-30 or IGHV3-33 | IGHJ6 | IGHD3-3 |
| VL | IGLV6-57 | IGLJ3 | |

SEQ ID NO: 25: TfR421 VL
DFMLTQPHSVSESPGKTVTISCTRSSGSIASNYVQWYQQRPGSSPTTVIY

EDNQRPSGVPDRFSGSIDSSSNSASLTISGLKTEDEADYYCQSYDSSNHW

VEGGGTKLAVL

SEQ ID NO: 26: TfR422 VL
DEMLTQPQSVSESPGKTVTISCTRSSGSIASNYVQWYQQRPGSSPTTVIY

EDNQRPSGVPDRFSGSIDSSSNSASLTISGLKTEDEADYYCQSYDSSNQW

VFGGGTKLAVL

SEQ ID NO: 46: TfR006 VL

SEQ ID NO: 47: IGLV6-57
NFMLTQPHSVSESPGKTVTISCTRSSGSIASNYVQWYQQRPGSSPTTVIY

EDNQRPSGVPDRFSGSIDSSSNSASLTISGLKTEDEADYYCQSYDSSN

Since IMGT Subgroup 6 has only one germline gene, it is impossible to obtain a consensus sequence. Thus, a consensus sequence was obtained by using Subgroup 6 together with Subgroups 1 and 2 (SEQ ID NO: 27). Based on this consensus sequence, modified bodies of the TfR006 antibody, TfR423 VL (SEQ ID NO: 28) and TfR424 VL (SEQ ID NO: 29), were prepared.

SEQ ID NO: 27: VL 1, 2, and 6 consensus sequence
QSxLTQPPSVSGSPGQSVTISCTGSSSNIGSxNyVSWYQQxPGtAPKLMI YENNKRPSGVPDRFSGSKxxSGNTASLTISGLQAEDEADYYCSSWDsSIS x SEQ ID NO: 28: TfR423 VL
DSALTQPPSVSGSPGQSVTISCTGSSSNIIASNSVQWYQQLPGtAPKTVI

YEDTQRPSGVPDRFSGSKDSSGNTASLTISGLQAEDEADYYCQSYDSAYH

WVFGGGTKLAVL

SEQ ID NO: 29: TfR424 VL
DSALTQPPSVSGSPGQSVTISCTGSSSNIIASNSVQWYQQLPGtAPKTVI

YENTQRPSGVPDRFSGSKDSSGNTASLTISGLQAEDEADYYCSSYDSAYH

WVFGGGTKLAVL

A human antibody VL that is closest to TfR006 VL is SUT (Accession No.: P06317, SEQ ID NO: 30). The two above VLs are different in a total of 15 amino acids in the amino acid sequence. Based on this information, the sequences of TfR425 VL (SEQ ID NO: 31) and TfR426 VL (SEQ ID NO: 32) were obtained according to a modification method similar to humanization technology.

SEQ ID NO: 30: SUT
DFMLTQPHSVSESPGKTVIISCTRSDGTIAGYYVQWYQQRPGRAPTTVIF

EDTQRPSGVPDRFSGSIDRSSNSASLTISGLQTEDEADYYCQSYDRDHWV

FGGGTKLTVLG

SEQ ID NO: 31: TfR425 VL
DFMLIQPHSVSESPGKTVIISCTRSDGTIAGYYVQWYQQRPGRAPTTVIF

EDTQRPSGVPDRFSGSIDRSSNSASLTISGLQTEDEADYYCQSYDSRDHW

VFGGGTKLTVL

SEQ ID NO: 32: TfR426 VL
DFMLTQPQSVSESPGKTVIISCTRSTGTIASNSVQWYQQRPGRAPTTVIF

DETQRPSGVPDRFSGSIDRSSNSASLTISGLQTEDEADYYCQSYDSRDQW

VFGGGTKLTVL (2) Modification of TfR006 Antibody L Chain

The CDR of the rambda chain of a TR006 antibody was grafted onto the consensus sequence (SEQ ID NO: 33) of subgroup I of the kappa chain to obtain the VL amino acid sequence of a TfR427 antibody (SEQ ID NO: 34). Moreover, a germline gene that is closest to this amino acid sequence, when it is converted to a nucleotide sequence, was searched on the IMTG database. As a result, it was found to be IGKV1-5. The CDR of the rambda chain of TfR006 was grafted on the frame of this IGKV1-5 (Accession No.: Z00001, SEQ ID NO: 35) to obtain the VL (SEQ ID NO: 36) of a TfR428 antibody. Furthermore, D92N and H95Q substitution were carried out on the CDR3 of VL of the TfR428 antibody, so as to obtain the VL sequences of a TfR429 antibody (SEQ ID NO: 37) and a TfR430 antibody (SEQ ID NO: 38).

SEQ ID NO: 33: Human KVI consensus sequence
DIQMTQSPSSLSASVGDRVTITCRASQSISNYLAWYQQKPGKAPKLLIYA

ASSLESGVPSRFSGSGSGTDFTLTISSLQPEDFATYYCQQYNSLPWTFGQ

GTKVEIK

```
SEQ ID NO: 34: TfR427 VL
DIQMTQSPSSLSASVGDRVTITCRASQIASNSVQWYQQKPGKAPKTVIYE

DTQLESGVPSRFSGSGSGTDFTLTISSLQPEDFATYYCQSYDSAYHWVFG

QGTKVEIK

SEQ ID NO: 35: IGKV1-5
DIQMTQSPSTLSASVGDRVTITCRASQSISSWLAWYQQKPGKAPKLLIYD

ASSLESGVPSRFSGSGSGTEFTLTISSLQPDDFATYYCQQYNSYS

SEQ ID NO: 36: TfR428 VL
DIQMTQSPSTLSASVGDRVTITCRASQIASNSVQWYQQKPGKAPKTVIYE

DTQLESGVPSRFSGSGSGIEFTLTISSLQPDDFATYYCQSYDSAYHWVFG

QGTKVEIK

SEQ ID NO: 37: TfR429 VL
DIQMTQSPSTLSASVGDRVTITCRASQIASNSVQWYQQKPGKAPKTVIYE

DTQLESGVPSRFSGSGSGIEFTLTISSLQPDDFATYYCQSYNSAYHWVFG

QGTKVEIK

SEQ ID NO: 38: TfR430 VL
DIQMTQSPSTLSASVGDRVTITCRASQIASNSVQWYQQKPGKAPKTVIYE

DTQLESGVPSRFSGSGSGIEFTLTISSLQPDDFATYYCQSYNSAYQWVFG

QGTKVEIK
```

A human κ chain which is close to the VL amino acid sequence of a TfR417 antibody is WEA (Accession No.: P01610, SEQ ID NO: 39). The CDR of the rambda chain of TfR006 was grafted on this frame. Thus, the VL sequence of a TfR431 antibody (SEQ ID NO: 40) was obtained. Moreover, D92N and H95A substitution were carried out on the CDR3 of a TfR431 antibody, so as to obtain the VL sequences of TfR432 and TfR433 antibodies.

```
SEQ ID NO: 39: WEA
DIQMTQSPSSLSASVGDRVTITCRASQGIRNDLTWYQQKPGTAPKRLIYG

ATSLQSGVPSRFSGSGSGTEFTLTINSLQPEDFATYYCLQYSSFPWTFGQ

GTKVEVK

SEQ ID NO: 40: TfR431 VL
DIQMTQSPSSLSASVGDRVTITCRASQIASNSVQWYQQKPGTAPKTVIYE

DTQLQSGVPSRFSGSGSGTEFTLTINSLQPEDFATYYCQSYDSAYHWVFG

QGTKVEIK

SEQ ID NO: 41: TfR432 VL
DIQMTQSPSSLSASVGDRVTITCRASQIASNSVQWYQQKPGTAPKTVIYE

DTQLQSGVPSRFSGSGSGTEFTLTINSLQPEDFATYYCQSYNSAYHWVFG

QGTKVEIK

SEQ ID NO: 42: TfR433 VL
DIQMTQSPSSLSASVGDRVTITCRASQIASNSVQWYQQKPGTAPKTVIYE

DTQLQSGVPSRFSGSGSGTEFTLTINSLQPEDFATYYCQSYNSAYQWVFG

QGTKVEIK
```

Example 5

Production of Each Modified Antibody (1) Production of Plasmid Expressing Each Modified TfR006 Antibody The above obtained TfR006 modified VH and VL were each ligated to a human G1 constant region (SEQ ID NO: 48) or to the corresponding L chain constant region (λ: SEQ ID NO: 49, and κ: SEQ ID NO: 50). H chain and L chain genes, to which NheI was added to the 5' side thereof and EcoRI was added to the 3' side thereof, were totally synthesized by GenScript. The thus synthesized heavy chain and light chain genes were each incorporated into different expression vectors. That is to say, artificially synthesized genes of the H chain and the L chain were each cleaved with NheI and EcoRI, and the cleavages were then incorporated into the NheI and EcoRI sites of the expression vector pCAGGS, so as to obtain a mutant antibody H chain expression vector and a mutant antibody L chain expression vector.

(2) Transient Expression of Modified TfR006 Antibody

FreeStyle (Life Technologies) was used for transient expression of a modified TfR006 antibody. 293-F (Life Technologies) used as floating cells for gene transfection was subcultured the day before transfection. On the day of transfection, 400 mL of a cell suspension whose cell density had been adjusted to be $1 \times 10^6$ cells/mL per antibody was prepared. Solution I was prepared by suspending a total of 200 μg of plasmid (100 μg of a TfR006 heavy chain expression vector of each antibody and 100 μg of a TfR006 light chain expression vector of each antibody) in OptiPro SFM. Subsequently, 200 μL of MAX reagent was added to 8 mL of OptiPRO (Solution II). Solution (I) was mixed with Solution (II), and the thus mixed solution was then left at rest at room temperature for 10 to 20 minutes. A total of 16 mL of the reaction solution was added to 400 mL of a 293 expression medium, in which the 293-F cells had been suspended, and the obtained mixture was then cultured at 37° C. in 8% $CO_2$ for 6 to 7 days, using a cell culture shaker TAITEC BioShaker BR-43FL. After 6 to 7 days of the culture, a culture supernatant containing a recombinant TfR006 antibody was recovered, and this was used as a material for purification.

(3) Purification of TfR006 IgG Antibody

Each antibody protein contained in a culture supernatant of the cell line transiently expressing the antibody was purified by using an Ab-Capcher ExTra (ProteNova) affinity column using AKTAprime. The obtained peak fraction was subjected to gel filtration using a Sephacryl S-300 column that had been equilibrated with Dalbecco's PBS as a solvent, so as to further purify it. The purified antibody protein was quantified using an absorption coefficient.

(4) Quantification of Antibody by Enzyme-Linked Immunosorbent Assay (ELISA)

The concentration of an antibody contained in a culture supernatant of TfR006 IgG antibody-producing cells and the concentration of a purified antibody were quantified based on absorbance, and was also quantified by enzyme-linked immunosorbent assay (ELISA). As a solid-phase antibody, goat anti-human IgG (H+L) (which had previously been absorbed against mouse, rabbit, bovine, and mouse IgG) (COMSO BIO: American Qualex International, Inc.; AQI, Cat. No. A-110UD) was added in an amount of 100 μl/well (concentration: 5 μg/mL) to a plate, and it was then left at rest at 4° C. over a day and a night. Subsequently, Block Ace was added in an amount of 200 μL/well to the plate to block the antibody at room temperature for 1 hour. Thereafter, the antibody as a sample was subjected to serial dilution, and it was then added to each well, followed by incubation for 1 hour for performing a reaction. The reaction product was washed with PBST (0.05% Tween 20 and PBS) five times, and then, a detection antibody solution prepared by 10,000 times diluting goat anti-human IgG (H+L) (absorbed against mouse, rabbit, bovine, and mouse IgG)-HRP (COSMO BIO: AQI, Cat. A-110PD) with PBST was added in an amount of 100 µL/well to the resultant. The obtained mixture was incubated for 1 hour, and was then washed with PBST five times. Thereafter, a substrate buffer TMB was added in an amount of 100 µL/well to the resultant. The obtained mixture was incubated at room temperature in a dark place for 15 minutes, and a reaction termination solution was then added thereto in an amount of 100 µL/well so as to terminate the reaction. Thereafter, the absorbance at 450 nm was measured. Using purified human IgG as a standard product, a calibration curve was obtained, and the concentration of a human antibody was calculated using this calibration curve.

Example 6

Reactivity of Modified TfR006 Antibody

TfR-expressing K562 cells (ATCC CCL-243: CML) were used to examine the reactivity of each modified antibody with an antigen. K562 cells were recovered by centrifugation, and were then washed with PBS once. Thereafter, the resulting cells were suspended in FACS Buffer (PBS containing 1% BSA, 2 mM EDTA, and 0.1% NaN3), resulting in a cell density of $1\times10^6$ cells/mL. 100 µL of this cell suspension was dispensed into a 96-well V bottom plate (Costar 3897). Thereafter, each antibody was adjusted to be 0.2 to 2 µg/mL with FACS Buffer, and 100 µL of each antibody solution was then added to the cells. The obtained mixture was incubated at 4° C. for 1 hour. Thereafter, the resulting cells were washed with FACS Buffer twice, and 100 µL of Alexa488-anti-human IgG (invitrogen) solution that had been 750 times diluted with FACS Buffer was then added to the cells. The thus obtained mixture was stirred and was then incubated at 4° C. for 1 hour. The resultant was washed by centrifugation with FACS Buffer twice, and was then equipped into HTS of FACS Calibur (BD), so as to measure the fluorescence intensity of FL1 in each well. As shown in FIG. 1, each modified antibodies (a: 1 ng/mL; b: 10 ng/mL; c: 100 ng/mL; and d: 1 µg/mL) exhibited reactivity with K562, which was equivalent to the reactivity of the parent antibody TfR006.

Example 7

In Vitro Cancer Cell Growth-Inhibiting Effect of Modified TLR Antibodies

Figure 2:
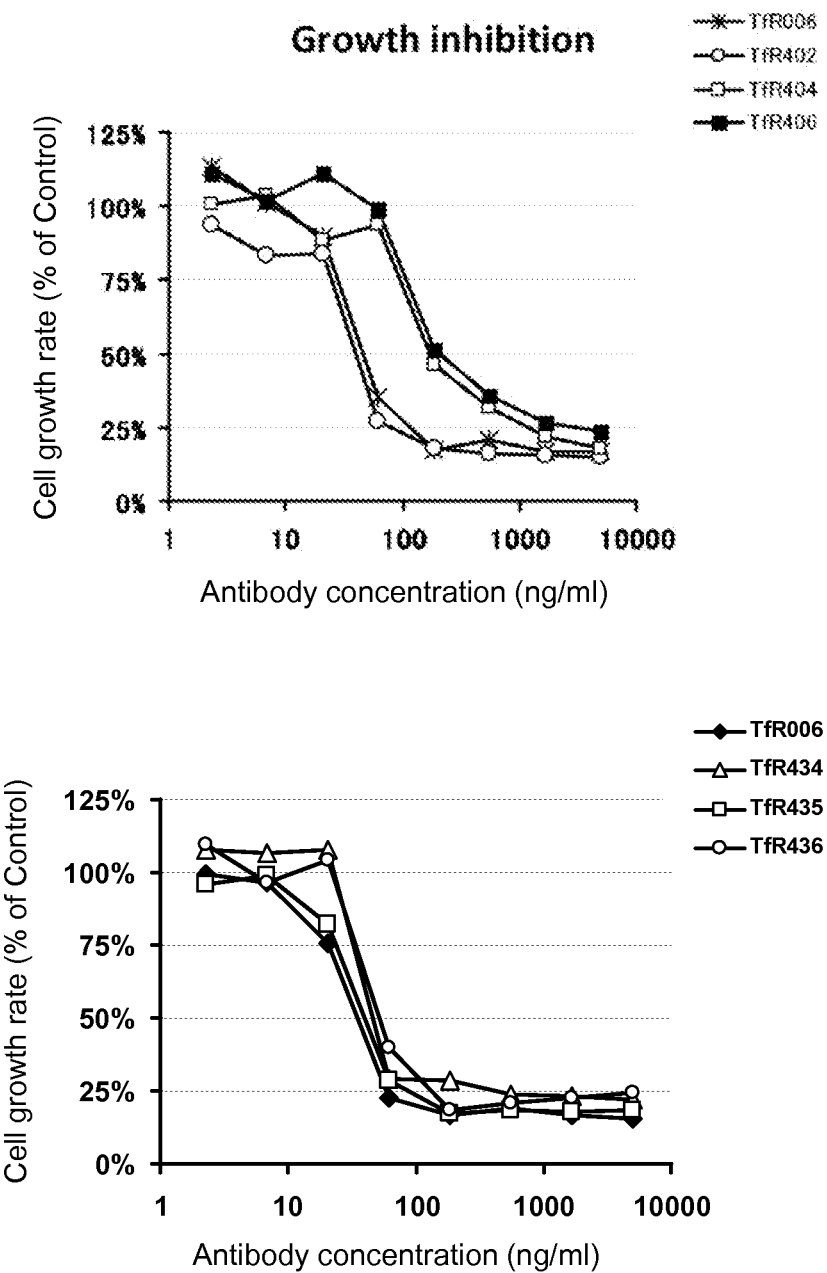
FIG. 2 shows the effects of each modified anti-TfR006 antibodies to inhibit the growth of K562 cells.

TfR-expressing cell line K-562 (ATCC CCL-243) or AIL cell line MT-2 was adjusted to a cell density of 2,500 cells/mL with a culture medium, and each cell solution was then dispensed in an amount of 100 µL/well into a 96-well flat bottom plate (NUNC 167008). Thereafter, a dilution series of each modified TfR006 antibodies (4.6 ng to 10 µg/mL) was prepared, and 100 µL of the prepared antibody was added to the cells. The cells were cultured at 37° C. in 5% $CO_2$ in 95% air for 96 hours. After completion of the culture, 200 µL of Cell Counting Kit (DOJINDO) was added to the plate, and the obtained mixture was then cultured at 37° C. in 5% $CO_2$ in 95% air for 3 hours. The absorbance at 450 nm was measured. The cell growth rate upon addition of the antibody in each concentration was calculated from the calculation formula below. Using Master Plex 2010 Software (Hitachi Solutions, Ltd.), an antibody concentration exhibiting a growth rate of 50% (IC50) was obtained (Table 7). As shown in FIG. 2, the modified TfR006 antibody inhibited the growth of cancer cells at almost the same level as the parent antibody.

Growth rate=antibody-added well value−blank(only culture media)/control value (antibody-not-added well)−blank(only culture media)×100%

TABLE 7

Antibody concentration exhibiting 50% growth rate (IC50)

| Antibody | TfRIC50 (ng/ml) | |
|---|---|---|
| | K562 | MT-2 |
| TfR006 | 34 | 8 |
| TfR402 | 41 | 9 |
| TfR404 | 175 | 19 |
| TfR406 | 206 | 21 |
| TfR434 | 39 | 8 |
| TfR435 | 38 | 10 |
| TfR436 | 39 | 11 |

Example 8

Antitumor Effects of Modified TfR Antibodies on ATL Cell Line Xenograft Models

The ATL cell line SU9T1 was cultured in an RPMI 1640 culture medium (SIGMA) supplemented with 10% FBS. For transplantation, the cells were recovered by centrifugation, and were then suspended in RPMI1640 to a cell density of $1\times10^8$ cells/mL. This cell suspension was mixed with the same amount of Matrigel (Becton, Dickinson and Company), and the obtained mixture was then transplanted into the subcutis on the right abdomen of each SCID mouse (female, 6-week-old, KYUDO CO., LTD.). After completion of the transplantation, the tumor diameter of each mouse was measured with a vernier caliper twice a week. At the time point at which the mean tumor volume reached approximately 150 $mm^3$, the mice were divided into some groups (five mice per group) according to random assignment regarding tumor volume. To the groups, each of TfR006, TfR402, TfR403, TfR404 and TfR406 antibodies was administered into the caudal vein of each mouse at an amount of 5 mg/kg group, and each of TfRTfR435 and TfR436 antibodies was administered into the caudal vein of each mouse at amounts of 10 mg/kg group and 3 mg/kg group. To a negative control group, PBS was administered at an amount of 0.2 mL/20 g mouse into the caudal vein of each mouse. Administration was carried out twice a week (every three or four days) in a total of five times. After completion of the administration, the tumor diameter was measured with a vernier caliper twice a week, and the tumor volume in each group was obtained, as in the case of before the assignment. Antitumor effects were determined based on the tumor volumes on the final day of measurement according to a parametric Dunnet's multiple comparison test, using the PBS group as a control.

Tumor volume was calculated according to the following formula.

Tumor volume=(Minor axis)$^2$×Major axis×0.5

The random assignment and the multiple comparison test were performed using animal experiment data statistical analysis software EXSUS (CLC Corporation).

Figure 4:
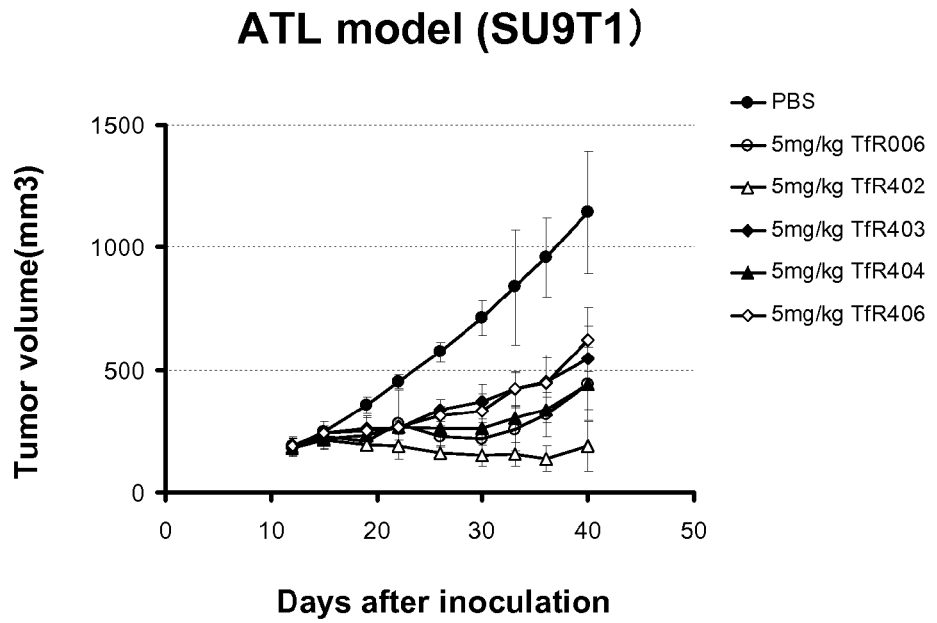
FIG. 4 shows the effects of modified anti-TfR006 antibodies to inhibit tumor growth in ATL models.
Figure 5:
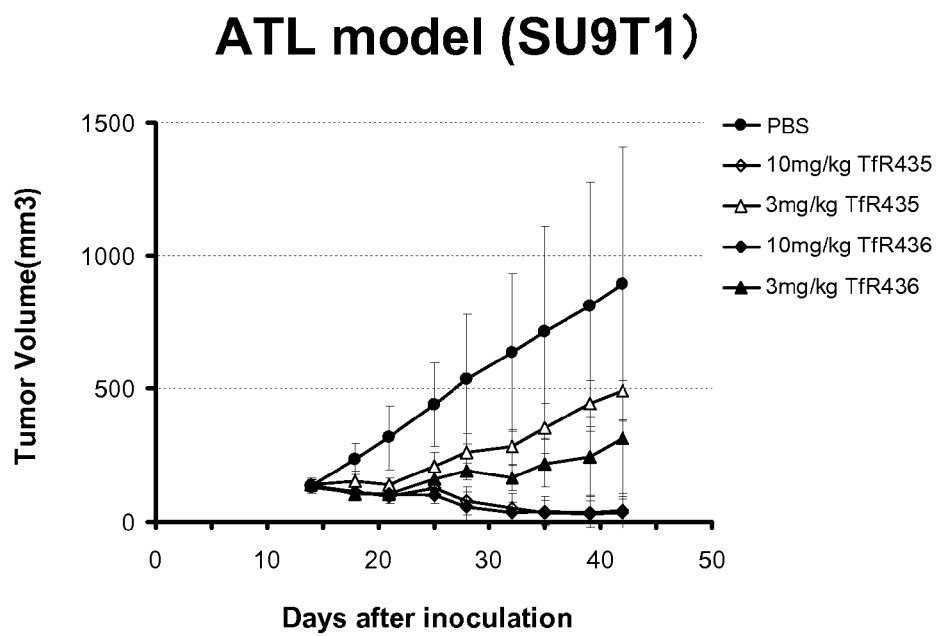
FIG. 5 shows the effects of modified anti-TfR006 antibodies to inhibit tumor growth in ATL models.

A change over time in a mean value of the tumor volumes in each group is shown in FIGS. 4 and 5. As shown in FIGS.

4 and 5, the growth of a tumor was inhibited by each TfR antibody administered. In particular, as shown in FIG. 4, the modified antibody TfR402 exhibited a stronger tumor growth-inhibiting effect than the parent antibody TfR006. The TfR435 and TfR436 antibodies did not only inhibit the growth of a tumor, but it also exhibited a significant tumor-reducing effect, at an amount of 10 mg/kg (FIG. 5).

Example 9

Antitumor Effects of Modified TfR Antibodies on Leukemia Xenograft Models

The leukemia cell line K562 (ATCC CCL-243) was cultured in an RPM 1640 culture medium supplemented with 10% FBS. For transplantation, the cells were recovered by centrifugation, and were then suspended in RPMI1640 to a cell density of $5 \times 10^7$ cells/mL. The obtained cancer cell suspension was transplanted in an amount of 100 µL/mouse into the subcutis on the right abdomen of each SCID mouse (female, 7-week-old, CLEA Japan, Inc.), resulting in an amount of $5 \times 10^6$ cells/mouse. After completion of the transplantation, the diameter of a tumor was measured with a vernier caliper, and the volume of the tumor was then obtained from the formula below. At the time point at which the mean tumor volume reached 150 mm³ or more, the mice were divided into some groups (n=5), using grouping software (EXSAS version 7.6, CLC Corporation). With regard to each antibody administration groups, the TfR006 antibody, TfR402 antibody, TfR404 antibody, TfR406 antibody, TfR435 antibody, and TfR436 antibody were administered at an amount of 5 mg/kg mouse into the caudal vein of each mouse. Moreover, with regard to low dose administration groups, the TfR402 antibody, TfR434 antibody, TfR435 antibody, and TfR436 antibody were administered at an amount of 1 mg/kg mouse into the caudal vein of each mouse. To a negative control group, PBS was administered at an amount of 0.2 mL/20 g mouse into the caudal vein of each mouse. Administration was carried out twice a week (every three or four days) in a total of five times. After completion of the administration, the tumor diameter was measured with a vernier caliper twice a week, and the tumor volume in each group was obtained. Antitumor effects were determined based on the tumor volumes.

Tumor volume was calculated according to the following formula.

$$\text{Tumor volume} = (\text{Minor axis})^2 \times \text{Major axis} \times 0.5$$

Figure 6:
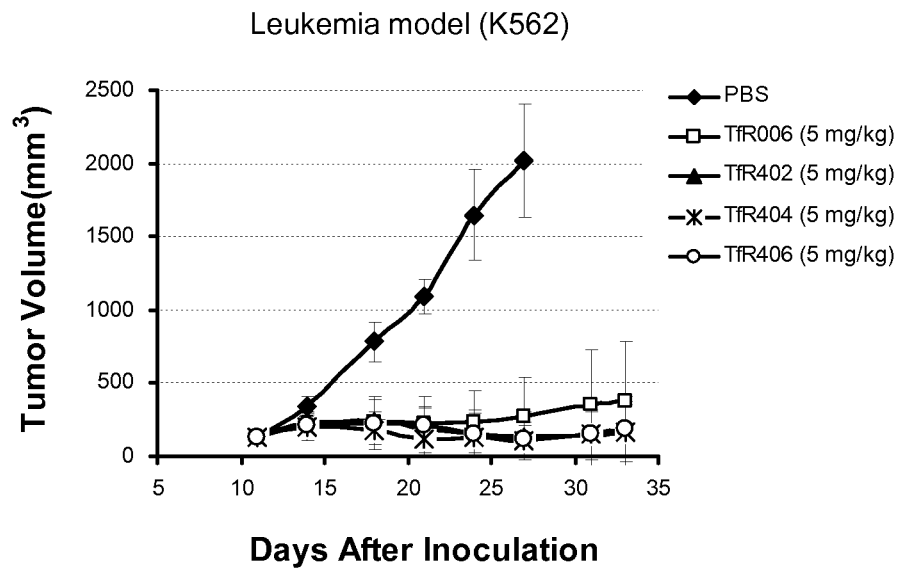
FIG. 6 shows the effects of modified anti-TfR006 antibodies to inhibit tumor growth in leukemia models.
Figure 7:
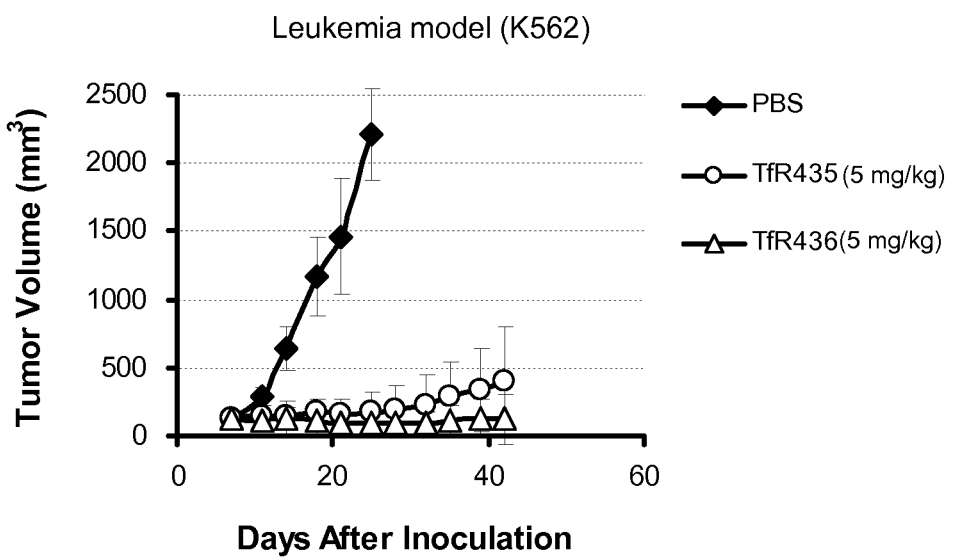
FIG. 7 shows the effects of modified anti-TfR006 antibodies to inhibit tumor growth in leukemia models.
Figure 8:
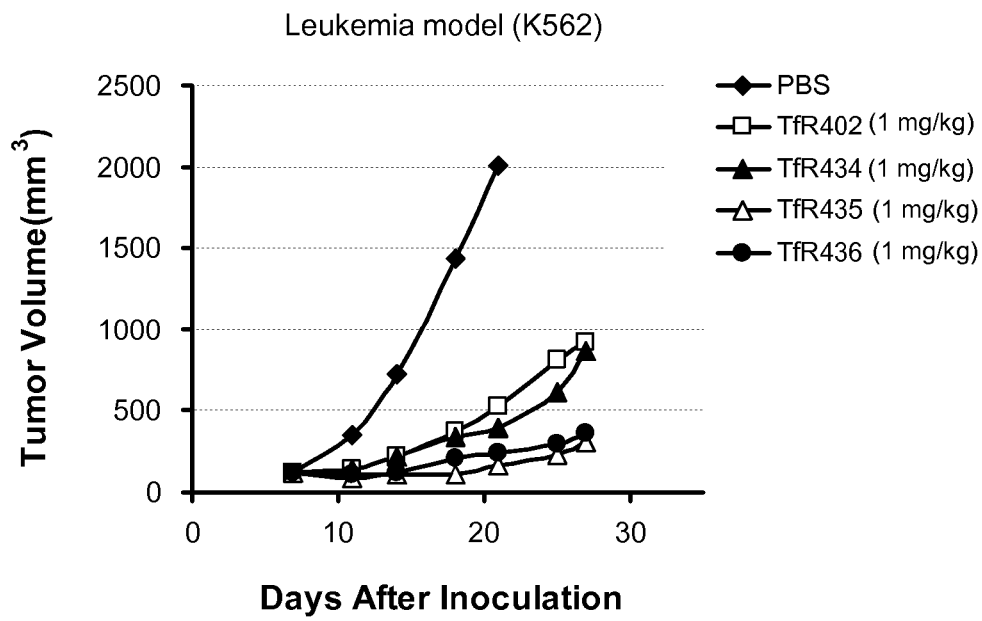
FIG. 8 shows the effects of modified anti-TfR006 antibodies to inhibit tumor growth in leukemia models.

A change over time in a mean value of the tumor volumes in each of the 5 mg/kg antibody administration groups is shown in FIGS. 6 and 7. As shown in FIGS. 6 and 7, the growth of a tumor was inhibited by each TfR antibody administered. In particular, as shown in FIG. 6, the modified antibodies TfR402 TfR404, and TfR406 all exhibited a stronger tumor growth-inhibiting effect than the parent antibody TfR006. It is particularly remarkable that the TfR435 and TfR436 antibodies significantly inhibited the growth of a tumor even at a low amount of 1 mg/kg (FIG. 8).

Example 10

Antitumor Effects of Modified TfR Antibodies on Solid Cancer Xenograft Models

The bladder cancer cell line BFTC-905 (DSMZ; ACC361) was cultured in a DMEM culture medium (SIGMA) supplemented with 10% FBS. For transplantation, the cells were recovered by centrifugation, and were then suspended in RPMI1640 to a cell density of $5 \times 10^7$ cells/mL. The obtained cancer cell suspension was transplanted in an amount of 100 µL/mouse into the subcutis on the right abdomen of each SCID mouse (female, 7-week-old, CLEA Japan, Inc.), resulting in an amount of $5 \times 10^6$ cells/mouse. After completion of the transplantation, the diameter of a tumor was measured with a vernier caliper, and the volume of the tumor was then obtained from the formula below. At the time point at which the mean tumor volume reached 200 mm³ or more, the mice were divided into some groups (n=5), using grouping software (EXSAS version 7.6, CLC Corporation). With regard to each antibody administration groups, the TfR435 antibody and TfR436 antibody were administered at an amount of 10 mg/kg mouse into the caudal vein of each mouse. To a negative control group, PBS was administered at an amount of 0.2 mL/20 g mouse into the caudal vein of each mouse. Administration was carried out twice a week (every three or four days) in a total of five times. After completion of the administration, the tumor diameter was measured with a vernier caliper twice a week, and the tumor volume in each group was obtained. Antitumor effects were determined based on the tumor volumes.

Tumor volume was calculated according to the following formula.

$$\text{Tumor volume} = (\text{Minor axis})^2 \times \text{Major axis} \times 0.5$$

Figure 9:
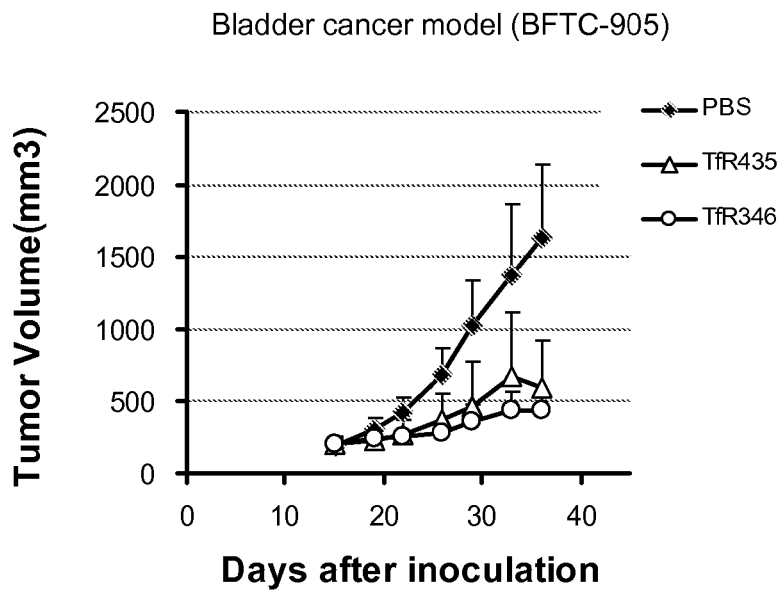
FIG. 9 shows the effects of modified anti-TfR006 antibodies to inhibit tumor growth in solid cancer models.

A change over time in a mean value of the tumor volumes in each antibody administration groups is shown in FIG. 9. As shown in FIG. 9, the growth of a tumor was inhibited by administration of the TfR435 and TfR436 antibodies.

Example 11

Construction of Plasmids Expressing IgG Antibodies of Antibodies 3TF12 and 3GH7 (WO 2011/073943)

WO 2011/073943 describes an scFv monomer and a dimeric antibody against human TfR. In order to compare the antibody of the present invention with the antibody described in WO 2011/073943, IgG1 antibodies of the 3TF12 and 3GH7 scFv antibodies described in WO 2011/073943 were prepared. The amino acid sequence and nucleotide sequence of 3TF12 scFv are shown in SEQ ID NOs: 55 and 56, respectively. The amino acid sequence and nucleotide sequence of 3GH7 scFv are shown in SEQ ID NOs: 57 and 58, respectively.

For production of the IgG1 antibodies, as in the case of the production of the antibody of the present invention, a method for producing antibodies, which comprises incorporating each of a heavy chain gene and a light chain gene into a different expression vector, and then co-transfecting two types of plasmids, namely, a heavy chain expression vector and a light chain expression vector upon gene introduction, was adopted.

Regarding a heavy chain, the nucleotide sequence of a variable region was inserted into a cassette vector, into which a human G1 gene had already been incorporated. Variable regions were the heavy chain variable region of 3TF12 scFv (amino acid sequence number: SEQ ID NO: 59; and nucleotide sequence number: SEQ ID NO: 60) and the heavy chain variable region of 3GH7 scFv (amino acid sequence number: SEQ ID NO: 61; and nucleotide sequence number: SEQ ID NO: 62).

Regarding a light chain, an entire light chain gene formed by connecting a constant region with a variable region was incorporated into an expression vector. Variable regions of the light chain were the light chain variable region of 3TF12 scFv (amino acid sequence number: SEQ ID NO: 63; and nucleotide sequence number: SEQ ID NO: 64) and the light chain variable region of 3GH7 scFv (amino acid sequence number: SEQ ID NO: 65; and nucleotide sequence number: SEQ ID NO: 66).

IGLC3*01 (GenBank Accession No.: J00254) that is a rambda constant region was connected with the nucleotide sequence of each variable region. The two N-terminal amino acids GQ (corresponding to GGTCAG in the nucleotide sequence), which had been confirmed to be deleted in Accession No. J00254 on the database, were added to the sequence (amino acid sequence number: SEQ ID NO: 67; and nucleotide sequence number: SEQ ID NO: 68).

Each gene was subjected to the optimization of the nucleotide sequence thereof, without changing the original amino acid sequence, and it was synthesized by GenScript. The amino acid sequence of the heavy chain variable region of the synthesized 3TF12 is shown in SEQ ID NO: 69, the optimized nucleotide sequence thereof is shown in SEQ ID NO: 70, the amino acid sequence of the light chain thereof is shown in SEQ ID NO: 71, and the optimized nucleotide sequence thereof is shown in SEQ ID NO: 72. The amino acid sequence of the heavy chain variable region of the synthesized 3GH7 is shown in SEQ ID NO: 73, the optimized nucleotide sequence thereof is shown in SEQ ID NO: 74, the amino acid sequence of the light chain thereof is shown in SEQ ID NO: 75, and the optimized nucleotide sequence thereof is shown in SEQ ID NO: 76. The amino acid sequence of the used human IGHG1 has been disclosed in Uniprot (P01857), and the amino acid sequence thereof is shown in SEQ ID NO: 77 and the nucleotide sequence thereof is shown in SEQ ID NO: 78. For the total synthesis of a gene, the restriction enzyme NheI recognition site was added to the 5 prime side of the synthesized gene and the restriction enzyme NheI recognition site was added to the 3 prime side thereof, for the convenience of construction. By treating the synthesized gene with these restriction enzymes, recombination of the antibody gene from a subcloning vector to an expression vector was carried out.

Example 12

Transient Expression of IgG Antibodies of Antibodies 3TF12 and 3GH7 (WO 2011/073943)

On the day before transfection, Expi293F cells (Life Technologies) were added at a cell density of $1.4 \times 10^6$ cells/mL to 85 mL of PowerCHO-2CD medium (LONZA) in an Erlenmeyer flask, and the obtained mixture was then subjected to shaking culture under conditions of 37° C. and 8% CO2, while setting the rotation number per minute (rpm) at 135.

Introduction of an antibody gene into Expi293F cells was carried out using two types of plasmids, namely, a heavy chain expression vector and a light chain expression vector.

For transfection into Expi293F cells, 50 μg of a heavy chain expression vector and 50 μg of a light chain expression vector were added to 5 mL of Opti-MEM (Life Technologies) in tube 1, and the obtained mixture was fully blended. Subsequently, 5 mL of Opti-MEM and 0.27 mL of Expi-Fectamine293 reagent were added to tube 2, and the obtained mixture was fully blended. The mixed solution in the tube 2 was added to the mixed solution in the tube 1, and the thus obtained mixed solution was stirred and was then left at rest at room temperature for 20 to 30 minutes. Thereafter, the mixture was added to Expi293F cells that had been subjected to shaking culture from the previous day (transfection). Sixteen to eighteen hours after the transfection, 0.5 mL of ExpiFectamine293 Transfection Enhancer 1 and 5 mL of ExpiFectamine293 Transfection Enhancer 2 were added to reaction solution. Thereafter, the obtained mixture was cultured at 37° C. in 8% CO2 at a rotation rate of 135 rpm for 6 days. Seven days after the transfection, a culture supernatant was recovered. The cells were removed by centrifugation, and the residue was then passed through a 0.2-μm filter. The resultant was used for purification of antibodies.

Example 13

Purification of IgG Antibodies of Antibodies 3TF12 and 3GH7 (WO 2011/073943)

Purification of antibodies was carried out, first using an anion-exchange carrier, and then using a protein A carrier. A culture supernatant of transient-expression Expi293F cells was purified using AKTAprime plus. The resulting supernatant was applied to CaptoQ (GE Healthcare) column (column volume: 10 mL) at a flow rate of 5 mL/min. The obtained fraction containing antibodies is a flow through fraction. However, since the nucleic acid (genome and RNA) as well as the protein bind to the anion-exchange carrier, so that they can be removed, it becomes possible to usefully utilize the binding capacity of the protein A. The obtained fraction was applied to a protein A carrier (Ab-Capcher ExTra: ProteNova; 10 mL) at a flow rate of 5 mL/min, and thereafter, D-PBS was used as a washing buffer at the same flow rate as that of the application of the fraction. The volume of an elution fraction was set at 4 mL/test tube, and fractionation was then carried out. Elution was carried out using a 0.1 M glycine-HCl buffer (pH 2.7) at a flow rate of 3 mL/min. 120 μL of a 1 M Tris-HCl buffer (pH 8.5) had previously been added to a test tube for fractioning the eluted solution, and at the same time as elution, the pH was promptly returned from an acidic range to a neutral range of around pH 6.5. The amount of a protein was detected at an absorbance of 280 nM, and a peak fraction was fractionated. This peak fraction was subjected to a Millipore stirring cell, in which an Ultracell Ultrafiltration Disk with a cutoff molecular weight of 30,000 was used, and the eluted solution was concentrated, while the buffer was exchanged with D-PBS.

Example 14

Affinity Comparison with 3TF12 and 3GH7 IgG Antibodies

The soluble TfR antigen prepared in Example 2 was suspended in an amount of 2 μg/mL in PBS (2.68 mM KCl, 1.47 mM $KH_2PO_4$, 136.89 mM NaCl, and 8.04 mM $Na_2HPO_4$), and the obtained suspension was then dispensed in a 96-well plate (Nunc Immunomodule MaxiSorp (Thermo Scientific, cat. 468667)) in an amount of 100 μL/well. It was then left at rest at 4° C. overnight.

On the following day, the solution in the well was discarded. A stock solution of Block Ace (DS Pharma Biomedical, cat. UK-B40) was dispensed in the plate in an amount of 200 μL/well, and it was then shaken at room temperature using a plate shaker (IKA, cat. MTS 2/4 digital) for 1 hour, so as to carry out blocking. Thereafter, the solution was discarded, and the plate was then washed (using a plate washer (Biotech, cat. MW-96AR) with 250 μL of Buffer A (PBS+0.05% Tween 20)×5 times). Subsequently, the purified antibodies TFR436, 3TF12 and 3GH7 were diluted with Buffer A to have different concentrations. The thus prepared solutions were each dispensed in the plate in an amount of 100 μL/well. It was then shaken at room temperature using a plate shaker for 1 hour.

The solution was discarded, and the plate was then washed. Thereafter, an HRP-labeled anti-human IgG antibody (Peroxidase-conjugated AffiniPure F(ab')$_2$ Fragment Goat Anti-Human IgG Fcγ Fragment Specific (Jackson ImmunoResearch, cat. 109-036-098)) was 50,000-fold diluted with Buffer A. The thus prepared solution was dispensed in the plate in an amount of 100 μL/well. It was then shaken at room temperature using a plate shaker for 1 hour.

After the plate had been washed, TMB coloring solution (SCYTEC, cat. TM4999) was added to the plate in an amount of 100 μL/well. It was then left at rest in a dark place for 8 minutes for the development of color. A stop solution (SCYTEC, cat. TSB999) was added to the plate in an amount of 100 μL/well, and the absorbance at 450 nm (A450) was then measured using a plate reader (CORONA ELECTRIC Co., Ltd., cat. MTP450)

Figure 10:
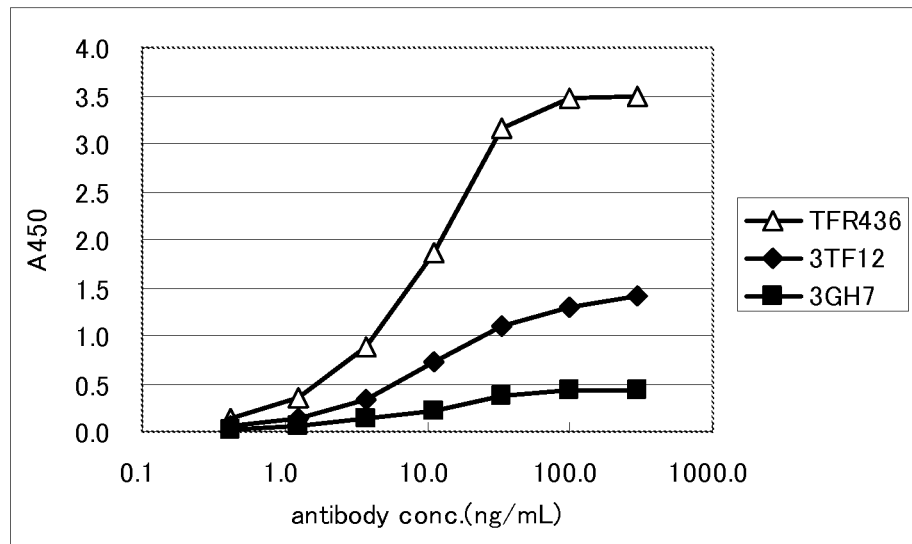
FIG. 10 shows the antigen-antibody ELISA effects of modified anti-TfR006 antibodies and prior antibodies.

The obtained results are shown in FIG. 10. As shown in FIG. 10, the TFR436 antibody exhibited significantly higher reactivity than 3TF12 and 3GH7. These results suggested that the TFR436 antibody had an affinity for the TFR antigen that was stronger than those of the 3TF12 and 3GH7 antibodies.

Example 15

Comparison with 3TF12 and 3GH7 IgG Antibodies in Terms of In Vivo Medicinal Effects The leukemia cell line K562 (ATCC CCL-243) was cultured in an RPMI 1640 culture medium supplemented with 10% FBS. For transplantation, the cells were recovered by centrifugation, and were then suspended in RPMI1640 to a cell density of $5\times10^7$ cells/mL. The obtained cancer cell suspension was transplanted in an amount of 100 μL/mouse into the subcutis on the right abdomen of each SCID mouse (female, 7-week-old, CLEA Japan, Inc.), resulting in an amount of $5\times10^6$ cells/mouse. After completion of the transplantation, the diameter of a tumor was measured with a vernier caliper, and the volume of the tumor was then obtained from the formula below. At the time point at which the mean tumor volume reached 150 mm$^3$ or more, the mice were divided into some groups (n=5), using grouping software (EXSAS version 7.6, CLC Corporation). With regard to each antibody administration groups, the TfR435 antibody, TfR436 antibody, 3TF12 antibody, and 3GH7T antibody were administered at an amount of 1 mg/kg into the caudal vein of each mouse. To a negative control group, PBS was administered at an amount of 0.2 mL/20 g mouse into the caudal vein of each mouse. Administration was carried out twice a week (every three or four days) in a total of five times. After completion of the administration, the tumor diameter was measured with a vernier caliper twice a week, and the tumor volume in each group was obtained. Antitumor effects were determined based on the tumor volumes.

Tumor volume was calculated according to the following formula.

Tumor volume=(Minor axis)$^2$×Major axis×0.5

Figure 11:
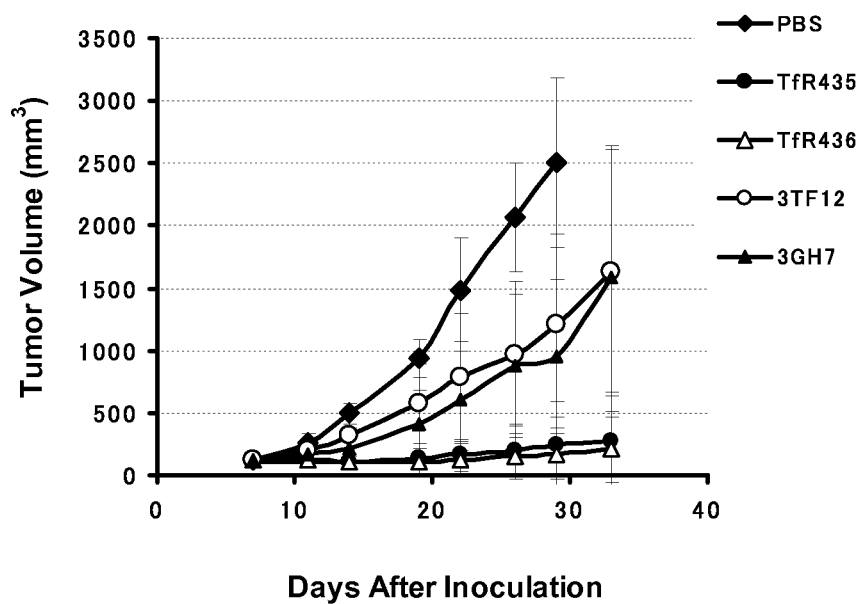
FIG. 11 shows the comparative results of the in vivo medicinal effects of modified anti-TfR006 antibodies and prior antibodies.

A change over time in a mean value of the tumor volumes in each antibody administration groups is shown in FIG. 11. As shown in FIG. 11, the growth of a tumor was significantly inhibited by administration of each of the TfR435 and TfR436 antibodies at an amount of 1 mg/kg. On the other hand, the 3TF12 and 3GH7 antibodies did not significantly inhibit the growth of a tumor.

The invention claimed is:

1. An antibody specifically reacting human transferring receptor (TfR), which is selected from the following (1) to (34):

(1) an antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 7, respectively, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively;

(2) an antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 8, respectively, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively;

(3) an antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 9, respectively, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively;

(4) an antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 10, respectively, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively;

(5) an antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 11, respectively, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively;

(6) an antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 12, respectively, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively;

(7) an antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 13, respectively, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively;

(8) an antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 14, respectively, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively;

(9) an antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 15, respectively, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively;

(10) an antibody, in which the heavy chain has SEQ ID NO: 16, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively;

(11) an antibody, in which the heavy chain has SEQ ID NO: 17, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively;

(12) an antibody, in which the heavy chain has SEQ ID NO: 18, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively;

(13) an antibody, in which the heavy chain has SEQ ID NO: 19, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively;

(14) an antibody, in which the heavy chain has SEQ ID NO: 20, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively;

(15) an antibody, in which the heavy chain has SEQ ID NO: 21, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively;

(16) an antibody, in which the heavy chain has SEQ ID NO: 22, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively;

(17) an antibody, in which the heavy chain has SEQ ID NO: 23, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively;

(18) an antibody, in which the heavy chain has SEQ ID NO: 24, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively;

(19) an antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 3, respectively, and the light chain variable region is shown in SEQ ID NO: 25;

(20) an antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 3, respectively, and the light chain variable region is shown in SEQ ID NO: 26;

(21) an antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 3, respectively, and the light chain variable region is shown in SEQ ID NO: 28;

(22) an antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 3, respectively, and the light chain variable region is shown in SEQ ID NO: 29;

(23) an antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 3, respectively, and the light chain variable region is shown in SEQ ID NO: 31;

(24) an antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 3, respectively, and the light chain variable region is shown in SEQ ID NO: 32;

(25) an antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 3, respectively, and the light chain variable region is shown in SEQ ID NO: 34;

(26) an antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 3, respectively, and the light chain variable region is shown in SEQ ID NO: 36;

(27) an antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 3, respectively, and the light chain variable region is shown in SEQ ID NO: 37;

(28) an antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 3, respectively, and the light chain variable region is shown in SEQ ID NO: 38;

(29) an antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 3, respectively, and the light chain variable region is shown in SEQ ID NO: 40;

(30) an antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 3, respectively, and the light chain variable region is shown in SEQ ID NO: 41;

(31) an antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 2, and 3, respectively, and the light chain variable region is shown in SEQ ID NO: 42;

(32) an antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 52, 3, respectively, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively;

(33) an antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 53, 3, respectively, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively; and

(34) an antibody, in which the heavy chain first complementarity determining region (VH CDR1), the heavy chain second complementarity determining region (VH CDR2), and the heavy chain third complementarity determining region (VH CDR3) are shown in SEQ ID NOs: 1, 54, 3, respectively, and the light chain first complementarity determining region (VL CDR1), the light chain second complementarity determining region (VL CDR2), and the light chain third complementarity determining region (VL CDR3) are shown in SEQ ID NOs: 4, 5, and 6, respectively.

2. The antibody of claim 1, wherein the antibody is a human antibody or a humanized antibody.

3. The antibody of claim 1, wherein the antibody is an antibody fragment selected from the group consisting of Fab, Fab', F(ab')$_2$, a single-chain antibody (scFv), a dimerized V region (Diabody), a disulfide-stabilized V region (dsFv), and a peptide comprising CDR.

4. A DNA encoding the antibody of claim 1.

5. A recombinant vector comprising the DNA of claim 4.

6. A transformed cell line which is obtained by introducing the recombinant vector of claim 5 into a host cell.

7. A method for producing the antibody of claim 1, said method comprising culturing a transformed cell line in a medium, then allowing the cell line to generate and accumulate the antibody in the culture, and then collecting the antibody from the culture,
wherein the transformed cell line is obtained by introducing a recombinant vector into a host cell, and
wherein the recombinant vector comprises a DNA encoding the antibody.

8. A pharmaceutical composition comprising the antibody of claim 1.

9. The pharmaceutical composition of claim 8, wherein a cytotoxic substance binds to the antibody.

10. The pharmaceutical composition of claim 9, wherein the cytotoxic substance is a drug, a toxin, or a radioactive substance.

11. The pharmaceutical composition of claim 8, which is used as an anticancer agent.

12. The pharmaceutical composition of claim 11, wherein the cancer is a blood cancer.

13. The pharmaceutical composition of claim 11, wherein the solid cancer is lung cancer, colon cancer, stomach cancer, bladder cancer, pancreatic cancer, prostate cancer, hepatic cancer, cervical cancer, ovarian cancer, breast cancer, or head and neck cancer.

14. The pharmaceutical composition of claim 11, wherein the blood cancer is leukemia, lymphoma, or myeloma.

15. The pharmaceutical composition of claim 11, wherein the blood cancer is adult T-cell leukemia (ATL).

16. The antibody of claim 2, wherein the antibody is an antibody fragment selected from the group consisting of Fab, Fab', F(ab')$_2$, a single-chain antibody (scFv), a dimerized V region (Diabody), a disulfide-stabilized V region (dsFv), and a peptide comprising CDR.

17. A DNA encoding the antibody of claim 2.
18. A DNA encoding the antibody of claim 3.
19. A recombinant vector comprising the DNA of claim 17.
20. A recombinant vector comprising the DNA of claim 18.

\* \* \* \* \*

SEQUENCE LISTING

```
<160> NUMBER OF SEQ ID NOS: 78

<210> SEQ ID NO 1
<211> LENGTH: 5
<212> TYPE: PRT
<213> ORGANISM: human

<400> SEQUENCE: 1

Ser Tyr Gly Met His
                  5

<210> SEQ ID NO 2
<211> LENGTH: 17
<212> TYPE: PRT
<213> ORGANISM: human

<400> SEQUENCE: 2

Val Ile Ser Phe Asp Gly Ser Ser Lys Tyr Tyr Ala Asp Ser Val Lys
1               5                   10                  15

Gly

<210> SEQ ID NO 3
<211> LENGTH: 14
<212> TYPE: PRT
<213> ORGANISM: human

<400> SEQUENCE: 3
```

```
Asp Ser Asn Phe Trp Ser Gly Tyr Tyr Ser Pro Val Asp Val
1               5                   10
```

```
<210> SEQ ID NO 4
<211> LENGTH: 13
<212> TYPE: PRT
<213> ORGANISM: human

<400> SEQUENCE: 4
```

```
Thr Arg Ser Ser Gly Ser Ile Ala Ser Asn Ser Val Gln
1               5                   10
```

```
<210> SEQ ID NO 5
<211> LENGTH: 8
<212> TYPE: PRT
<213> ORGANISM: human

<400> SEQUENCE: 5
```

```
Tyr Glu Asp Thr Gln Arg Pro Ser
1               5
```

```
<210> SEQ ID NO 6
<211> LENGTH: 10
<212> TYPE: PRT
<213> ORGANISM: human

<400> SEQUENCE: 6
```

```
Gln Ser Tyr Asp Ser Ala Tyr His Trp Val
1               5                   10
```

```
<210> SEQ ID NO 7
<211> LENGTH: 14
<212> TYPE: PRT
<213> ORGANISM: human

<400> SEQUENCE: 7
```

```
Asp Gly Asn Phe Trp Ser Gly Tyr Tyr Ser Pro Val Asp Val
1               5                   10
```

```
<210> SEQ ID NO 8
<211> LENGTH: 14
<212> TYPE: PRT
<213> ORGANISM: human

<400> SEQUENCE: 8
```

```
Asp Ser Ala Phe Trp Ser Gly Tyr Tyr Ser Pro Val Asp Val
1               5                   10
```

```
<210> SEQ ID NO 9
<211> LENGTH: 14
<212> TYPE: PRT
<213> ORGANISM: human

<400> SEQUENCE: 9
```

```
Asp Ser Asn Leu Trp Ser Gly Tyr Tyr Ser Pro Val Asp Val
1               5                   10
```

```
<210> SEQ ID NO 10
<211> LENGTH: 14
<212> TYPE: PRT
<213> ORGANISM: human

<400> SEQUENCE: 10
```

```
Asp Ser Asn Phe Trp Gly Gly Tyr Tyr Ser Pro Val Asp Val
```

<210> SEQ ID NO 11
<211> LENGTH: 14
<212> TYPE: PRT
<213> ORGANISM: human

<400> SEQUENCE: 11

Asp Ser Ala Leu Trp Gly Gly Tyr Tyr Ser Pro Val Asp Val
1               5                   10

<210> SEQ ID NO 12
<211> LENGTH: 14
<212> TYPE: PRT
<213> ORGANISM: human

<400> SEQUENCE: 12

Asp Gly Asn Leu Trp Gly Gly Tyr Tyr Ser Pro Val Asp Val
1               5                   10

<210> SEQ ID NO 13
<211> LENGTH: 14
<212> TYPE: PRT
<213> ORGANISM: human

<400> SEQUENCE: 13

Asp Gly Ala Phe Trp Gly Gly Tyr Tyr Ser Pro Val Asp Val
1               5                   10

<210> SEQ ID NO 14
<211> LENGTH: 14
<212> TYPE: PRT
<213> ORGANISM: human

<400> SEQUENCE: 14

Asp Gly Ala Leu Trp Ser Gly Tyr Tyr Ser Pro Val Asp Val
1               5                   10

<210> SEQ ID NO 15
<211> LENGTH: 14
<212> TYPE: PRT
<213> ORGANISM: human

<400> SEQUENCE: 15

Asp Gly Ala Leu Trp Gly Gly Tyr Tyr Ser Pro Val Asp Val
1               5                   10

<210> SEQ ID NO 16
<211> LENGTH: 122
<212> TYPE: PRT
<213> ORGANISM: human

<400> SEQUENCE: 16

Asp Val Gln Leu Val Glu Ser Gly Gly Leu Val Gln Pro Gly Gly
1               5                   10                  15

Ser Leu Arg Leu Ser Cys Ala Ala Ser Gly Phe Pro Phe Lys Ser Tyr
                20                  25                  30

Gly Met Gln Trp Val Arg Gln Ala Pro Gly Lys Gly Leu Glu Trp Val
            35                  40                  45

Ala Val Ile Ser Phe Asp Gly Ser Ser Arg Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asp Gly Ala Leu Trp Gly Gly Tyr Tyr Ser Pro Val Asp Val
            100                 105                 110

Trp Gly Gln Gly Thr Leu Val Thr Val Ser
        115                 120

<210> SEQ ID NO 17
<211> LENGTH: 123
<212> TYPE: PRT
<213> ORGANISM: human

<400> SEQUENCE: 17

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Phe Lys Ser Tyr
            20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asp Gly Ala Leu Trp Gly Gly Tyr Tyr Ser Pro Val Asp Val
            100                 105                 110

Trp Gly Gln Gly Thr Leu Val Thr Val Ser Ser
        115                 120

<210> SEQ ID NO 18
<211> LENGTH: 123
<212> TYPE: PRT
<213> ORGANISM: human

<400> SEQUENCE: 18

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Phe Lys Ser Tyr
            20                  25                  30

Ala Met His Trp Val Arg Gln Ala Pro Gly Lys Gly Leu Glu Trp Val
            35                  40                  45

Ala Val Ile Ser Phe Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asp Gly Ala Leu Trp Gly Gly Tyr Tyr Ser Pro Val Asp Val
            100                 105                 110

Trp Gly Gln Gly Thr Leu Val Thr Val Ser Ser
        115                 120

<210> SEQ ID NO 19
<211> LENGTH: 123
<212> TYPE: PRT
<213> ORGANISM: human

-continued

```
<400> SEQUENCE: 19

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Phe Lys Ser Tyr
            20                  25                  30

Ala Met His Trp Val Arg Gln Ala Pro Gly Lys Gly Leu Glu Trp Val
        35                  40                  45

Ala Val Ile Ser Phe Asp Gly Ser Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ala Leu Trp Gly Gly Tyr Tyr Ser Pro Val Asp Val
            100                 105                 110

Trp Gly Gln Gly Thr Leu Val Thr Val Ser Ser
            115                 120

<210> SEQ ID NO 20
<211> LENGTH: 123
<212> TYPE: PRT
<213> ORGANISM: human

<400> SEQUENCE: 20

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Phe Lys Ser Tyr
            20                  25                  30

Gly Met Gln Trp Val Arg Gln Ala Pro Gly Lys Gly Leu Glu Trp Val
        35                  40                  45

Ala Val Ile Ser Phe Asp Gly Ser Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ala Leu Trp Gly Gly Tyr Tyr Ser Pro Val Asp Val
            100                 105                 110

Trp Gly Gln Gly Thr Leu Val Thr Val Ser Ser
            115                 120

<210> SEQ ID NO 21
<211> LENGTH: 123
<212> TYPE: PRT
<213> ORGANISM: human

<400> SEQUENCE: 21

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gln Trp Val Arg Gln Ala Pro Gly Lys Gly Leu Glu Trp Val
        35                  40                  45

Ala Val Ile Ser Phe Asp Gly Ser Arg Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gly Ala Leu Trp Gly Gly Tyr Tyr Ser Pro Val Asp Val
            100                 105                 110

Trp Gly Gln Gly Thr Leu Val Thr Val Ser Ser
            115                 120
```

<210> SEQ ID NO 22
<211> LENGTH: 123
<212> TYPE: PRT
<213> ORGANISM: human

<400> SEQUENCE: 22

```
Asp Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Gly Met Gln Trp Val Arg Gln Ala Pro Gly Lys Gly Leu Glu Trp Val
             35                  40                  45

Ala Val Ile Ser Phe Asp Gly Ser Arg Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gly Ala Leu Trp Gly Gly Tyr Tyr Ser Pro Val Asp Val
            100                 105                 110

Trp Gly Gln Gly Thr Leu Val Thr Val Ser Ser
            115                 120
```

<210> SEQ ID NO 23
<211> LENGTH: 123
<212> TYPE: PRT
<213> ORGANISM: human

<400> SEQUENCE: 23

```
Asp Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Ala Met Gln Trp Val Arg Gln Ala Pro Gly Lys Gly Leu Glu Trp Val
             35                  40                  45

Ser Val Ile Ser Phe Asp Gly Asn Arg Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gly Ala Leu Trp Gly Gly Tyr Tyr Ser Pro Val Asp Val
            100                 105                 110

Trp Gly Gln Gly Thr Leu Val Thr Val Ser Ser
            115                 120
```

<210> SEQ ID NO 24
<211> LENGTH: 123

```
<212> TYPE: PRT
<213> ORGANISM: human

<400> SEQUENCE: 24

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gln Trp Val Arg Gln Ala Pro Gly Lys Gly Leu Glu Trp Val
        35                  40                  45

Ser Ile Val Ser Phe Asp Gly Gly Asn Arg Tyr Tyr Ala Asp Ser Ile
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ala Leu Trp Gly Gly Tyr Tyr Ser Pro Ile Asp Val
            100                 105                 110

Trp Gly Gln Gly Thr Leu Val Thr Val Ser Ser
        115                 120

<210> SEQ ID NO 25
<211> LENGTH: 111
<212> TYPE: PRT
<213> ORGANISM: human

<400> SEQUENCE: 25

Asp Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn His Trp Val Phe Gly Gly Gly Thr Lys Leu Ala Val Leu
            100                 105                 110

<210> SEQ ID NO 26
<211> LENGTH: 111
<212> TYPE: PRT
<213> ORGANISM: human

<400> SEQUENCE: 26

Asp Phe Met Leu Thr Gln Pro Gln Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
```

```
              65                  70                  75                  80
Leu Lys Thr Glu Asp Glu Ala Asp Tyr Tyr Cys Gln Ser Tyr Asp Ser
                    85                  90                  95

Ser Asn Gln Trp Val Phe Gly Gly Gly Thr Lys Leu Ala Val Leu
                100                 105                 110
```

<210> SEQ ID NO 27
<211> LENGTH: 101
<212> TYPE: PRT
<213> ORGANISM: human
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (69)..(70)
<223> OTHER INFORMATION: Xaa can be any naturally occurring amino acid
<220> FEATURE:
<221> NAME/KEY: misc_feature
<222> LOCATION: (101)..(101)
<223> OTHER INFORMATION: Xaa can be any naturally occurring amino acid

<400> SEQUENCE: 27

```
Gln Ser Xaa Leu Thr Gln Pro Pro Ser Val Ser Gly Ser Pro Gly Gln
1               5                   10                  15

Ser Val Thr Ile Ser Cys Thr Gly Ser Ser Ser Asn Ile Gly Ser Xaa
                20                  25                  30

Asn Tyr Val Ser Trp Tyr Gln Gln Xaa Pro Gly Thr Ala Pro Lys Leu
                35                  40                  45

Met Ile Tyr Glu Asn Asn Lys Arg Pro Ser Gly Val Pro Asp Arg Phe
            50                  55                  60

Ser Gly Ser Lys Xaa Xaa Ser Gly Asn Thr Ala Ser Leu Thr Ile Ser
65                  70                  75                  80

Gly Leu Gln Ala Glu Asp Glu Ala Asp Tyr Tyr Cys Ser Ser Trp Asp
                85                  90                  95

Ser Ser Leu Ser Xaa
            100
```

<210> SEQ ID NO 28
<211> LENGTH: 112
<212> TYPE: PRT
<213> ORGANISM: human

<400> SEQUENCE: 28

```
Asp Ser Ala Leu Thr Gln Pro Pro Ser Val Ser Gly Ser Pro Gly Gln
1               5                   10                  15

Ser Val Thr Ile Ser Cys Thr Gly Ser Ser Ser Asn Ile Ile Ala Ser
                20                  25                  30

Asn Ser Val Gln Trp Tyr Gln Gln Leu Pro Gly Thr Ala Pro Lys Thr
                35                  40                  45

Val Ile Tyr Glu Asp Thr Gln Arg Pro Ser Gly Val Pro Asp Arg Phe
            50                  55                  60

Ser Gly Ser Lys Asp Ser Ser Gly Asn Thr Ala Ser Leu Thr Ile Ser
65                  70                  75                  80
```

```
Gly Leu Gln Ala Glu Asp Glu Ala Asp Tyr Tyr Cys Gln Ser Tyr Asp
                85                  90                  95

Ser Ala Tyr His Trp Val Phe Gly Gly Gly Thr Lys Leu Ala Val Leu
            100                 105                 110

<210> SEQ ID NO 29
<211> LENGTH: 112
<212> TYPE: PRT
<213> ORGANISM: human

<400> SEQUENCE: 29

Asp Ser Ala Leu Thr Gln Pro Pro Ser Val Ser Gly Ser Pro Gly Gln
1               5                   10                  15

Ser Val Thr Ile Ser Cys Thr Gly Ser Ser Ser Asn Ile Ile Ala Ser
            20                  25                  30

Asn Ser Val Gln Trp Tyr Gln Gln Leu Pro Gly Thr Ala Pro Lys Thr
            35                  40                  45

Val Ile Tyr Glu Asn Thr Gln Arg Pro Ser Gly Val Pro Asp Arg Phe
        50                  55                  60

Ser Gly Ser Lys Asp Ser Ser Gly Asn Thr Ala Ser Leu Thr Ile Ser
65                  70                  75                  80

Gly Leu Gln Ala Glu Asp Glu Ala Asp Tyr Tyr Cys Ser Ser Tyr Asp
                85                  90                  95

Ser Ala Tyr His Trp Val Phe Gly Gly Gly Thr Lys Leu Ala Val Leu
            100                 105                 110

<210> SEQ ID NO 30
<211> LENGTH: 111
<212> TYPE: PRT
<213> ORGANISM: human

<400> SEQUENCE: 30

Asp Phe Met Leu Thr Gln Pro His Ser Val Ser Glu Ser Pro Gly Lys
1               5                   10                  15

Thr Val Ile Ile Ser Cys Thr Arg Ser Asp Gly Thr Ile Ala Gly Tyr
            20                  25                  30

Tyr Val Gln Trp Tyr Gln Gln Arg Pro Gly Arg Ala Pro Thr Thr Val
            35                  40                  45

Ile Phe Glu Asp Thr Gln Arg Pro Ser Gly Val Pro Asp Arg Phe Ser
        50                  55                  60

Gly Ser Ile Asp Arg Ser Ser Asn Ser Ala Ser Leu Thr Ile Ser Gly
65                  70                  75                  80

Leu Gln Thr Glu Asp Glu Ala Asp Tyr Tyr Cys Gln Ser Tyr Asp Arg
                85                  90                  95

Asp His Trp Val Phe Gly Gly Gly Thr Lys Leu Thr Val Leu Gly
            100                 105                 110

<210> SEQ ID NO 31
<211> LENGTH: 111
<212> TYPE: PRT
<213> ORGANISM: human

<400> SEQUENCE: 31

Asp Phe Met Leu Thr Gln Pro His Ser Val Ser Glu Ser Pro Gly Lys
1               5                   10                  15

Thr Val Ile Ile Ser Cys Thr Arg Ser Asp Gly Thr Ile Ala Gly Tyr
            20                  25                  30
```

-continued

Tyr Val Gln Trp Tyr Gln Gln Arg Pro Gly Arg Ala Pro Thr Thr Val
            35                  40                  45

Ile Phe Glu Asp Thr Gln Arg Pro Ser Gly Val Pro Asp Arg Phe Ser
 50                  55                  60

Gly Ser Ile Asp Arg Ser Ser Asn Ser Ala Ser Leu Thr Ile Ser Gly
 65                  70                  75                  80

Leu Gln Thr Glu Asp Glu Ala Asp Tyr Tyr Cys Gln Ser Tyr Asp Ser
                 85                  90                  95

Arg Asp His Trp Val Phe Gly Gly Gly Thr Lys Leu Thr Val Leu
                100                 105                 110

<210> SEQ ID NO 32
<211> LENGTH: 111
<212> TYPE: PRT
<213> ORGANISM: human

<400> SEQUENCE: 32

Asp Phe Met Leu Thr Gln Pro Gln Ser Val Ser Glu Ser Pro Gly Lys
 1               5                  10                  15

Thr Val Ile Ile Ser Cys Thr Arg Ser Thr Gly Thr Ile Ala Ser Asn
                20                  25                  30

Ser Val Gln Trp Tyr Gln Gln Arg Pro Gly Arg Ala Pro Thr Thr Val
            35                  40                  45

Ile Phe Asp Glu Thr Gln Arg Pro Ser Gly Val Pro Asp Arg Phe Ser
 50                  55                  60

Gly Ser Ile Asp Arg Ser Ser Asn Ser Ala Ser Leu Thr Ile Ser Gly
 65                  70                  75                  80

Leu Gln Thr Glu Asp Glu Ala Asp Tyr Tyr Cys Gln Ser Tyr Asp Ser
                 85                  90                  95

Arg Asp Gln Trp Val Phe Gly Gly Gly Thr Lys Leu Thr Val Leu
                100                 105                 110

<210> SEQ ID NO 33
<211> LENGTH: 107
<212> TYPE: PRT
<213> ORGANISM: human

<400> SEQUENCE: 33

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Asn Tyr
                20                  25                  30

Leu Ala Trp Tyr Gln Gln Lys Pro Gly Lys Ala Pro Lys Leu Leu Ile
            35                  40                  45

Tyr Ala Ala Ser Ser Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Leu Pro Trp
                 85                  90                  95

Thr Phe Gly Gln Gly Thr Lys Val Glu Ile Lys
                100                 105

<210> SEQ ID NO 34
<211> LENGTH: 108
<212> TYPE: PRT
<213> ORGANISM: human

```
<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ile Ala Ser Asn Ser
            20                  25                  30

Val Gln Trp Tyr Gln Gln Lys Pro Gly Lys Ala Pro Lys Thr Val Ile
        35                  40                  45

Tyr Glu Asp Thr Gln Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Tyr Asp Ser Ala Tyr His
                85                  90                  95

Trp Val Phe Gly Gln Gly Thr Lys Val Glu Ile Lys
                100                 105

<210> SEQ ID NO 35
<211> LENGTH: 95
<212> TYPE: PRT
<213> ORGANISM: human

<400> SEQUENCE: 35

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser
                85                  90                  95

<210> SEQ ID NO 36
<211> LENGTH: 108
<212> TYPE: PRT
<213> ORGANISM: human

<400> SEQUENCE: 36

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ile Ala Ser Asn Ser
            20                  25                  30

Val Gln Trp Tyr Gln Gln Lys Pro Gly Lys Ala Pro Lys Thr Val Ile
        35                  40                  45

Tyr Glu Asp Thr Gln Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Ser Tyr Asp Ser Ala Tyr His
                85                  90                  95

Trp Val Phe Gly Gln Gly Thr Lys Val Glu Ile Lys
                100                 105
```

<210> SEQ ID NO 37
<211> LENGTH: 108
<212> TYPE: PRT
<213> ORGANISM: human

<400> SEQUENCE: 37

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ile Ala Ser Asn Ser
            20                  25                  30

Val Gln Trp Tyr Gln Gln Lys Pro Gly Lys Ala Pro Lys Thr Val Ile
        35                  40                  45

Tyr Glu Asp Thr Gln Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Ser Tyr Asn Ser Ala Tyr His
                85                  90                  95

Trp Val Phe Gly Gln Gly Thr Lys Val Glu Ile Lys
            100                 105

<210> SEQ ID NO 38
<211> LENGTH: 108
<212> TYPE: PRT
<213> ORGANISM: human

<400> SEQUENCE: 38

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ile Ala Ser Asn Ser
            20                  25                  30

Val Gln Trp Tyr Gln Gln Lys Pro Gly Lys Ala Pro Lys Thr Val Ile
        35                  40                  45

Tyr Glu Asp Thr Gln Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Ser Tyr Asn Ser Ala Tyr Gln
                85                  90                  95

Trp Val Phe Gly Gln Gly Thr Lys Val Glu Ile Lys
            100                 105

<210> SEQ ID NO 39
<211> LENGTH: 107
<212> TYPE: PRT
<213> ORGANISM: human

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Thr Trp Tyr Gln Gln Lys Pro Gly Thr Ala Pro Lys Arg Leu Ile
        35                  40                  45

Tyr Gly Ala Thr Ser Leu Gln Ser Gly Val Pro Ser Arg Phe Ser Gly
    50                  55                  60

Ser Gly Ser Gly Thr Glu Phe Thr Leu Thr Ile Asn Ser Leu Gln Pro
65                  70                  75                  80

-continued

```
Glu Asp Phe Ala Thr Tyr Tyr Cys Leu Gln Tyr Ser Ser Phe Pro Trp
                85                  90                  95

Thr Phe Gly Gln Gly Thr Lys Val Glu Val Lys
            100                 105

<210> SEQ ID NO 40
<211> LENGTH: 108
<212> TYPE: PRT
<213> ORGANISM: human

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ile Ala Ser Asn Ser
            20                  25                  30

Val Gln Trp Tyr Gln Gln Lys Pro Gly Thr Ala Pro Lys Thr Val Ile
        35                  40                  45

Tyr Glu Asp Thr Gln Leu Gln Ser Gly Val Pro Ser Arg Phe Ser Gly
    50                  55                  60

Ser Gly Ser Gly Thr Glu Phe Thr Leu Thr Ile Asn Ser Leu Gln Pro
65                  70                  75                  80

Glu Asp Phe Ala Thr Tyr Tyr Cys Gln Ser Tyr Asp Ser Ala Tyr His
                85                  90                  95

Trp Val Phe Gly Gln Gly Thr Lys Val Glu Ile Lys
            100                 105

<210> SEQ ID NO 41
<211> LENGTH: 108
<212> TYPE: PRT
<213> ORGANISM: human

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ile Ala Ser Asn Ser
            20                  25                  30

Val Gln Trp Tyr Gln Gln Lys Pro Gly Thr Ala Pro Lys Thr Val Ile
        35                  40                  45

Tyr Glu Asp Thr Gln Leu Gln Ser Gly Val Pro Ser Arg Phe Ser Gly
    50                  55                  60

Ser Gly Ser Gly Thr Glu Phe Thr Leu Thr Ile Asn Ser Leu Gln Pro
65                  70                  75                  80

Glu Asp Phe Ala Thr Tyr Tyr Cys Gln Ser Tyr Asn Ser Ala Tyr His
                85                  90                  95

Trp Val Phe Gly Gln Gly Thr Lys Val Glu Ile Lys
            100                 105

<210> SEQ ID NO 42
<211> LENGTH: 108
<212> TYPE: PRT
<213> ORGANISM: human

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ile Ala Ser Asn Ser
            20                  25                  30
```

```
Val Gln Trp Tyr Gln Gln Lys Pro Gly Thr Ala Pro Lys Thr Val Ile
         35                  40                  45

Tyr Glu Asp Thr Gln Leu Gln Ser Gly Val Pro Ser Arg Phe Ser Gly
 50                  55                  60

Ser Gly Ser Gly Thr Glu Phe Thr Leu Thr Ile Asn Ser Leu Gln Pro
 65                  70                  75                  80

Glu Asp Phe Ala Thr Tyr Tyr Cys Gln Ser Tyr Asn Ser Ala Tyr Gln
                 85                  90                  95

Trp Val Phe Gly Gln Gly Thr Lys Val Glu Ile Lys
                100                 105
```

<210> SEQ ID NO 43
<211> LENGTH: 123
<212> TYPE: PRT
<213> ORGANISM: human

<400> SEQUENCE: 43

```
Gln Val Gln Leu Val Gln Ser Gly Gly Val Val Gln Pro Gly Arg
 1               5                  10                  15

Ser Leu Arg Leu Ser Cys Ala Ala Ser Gly Phe Pro Phe Lys Ser Tyr
                 20                  25                  30

Gly Met His Trp Val Arg Gln Ala Pro Gly Lys Gly Leu Glu Trp Val
             35                  40                  45

Ala Val Ile Ser Phe Asp Gly Ser Ser Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Gly Glu Asp Thr Ala Val Tyr Tyr Cys
                 85                  90                  95

Ala Arg Asp Ser Asn Phe Trp Ser Gly Tyr Tyr Ser Pro Val Asp Val
                100                 105                 110

Trp Gly Gln Gly Thr Thr Val Thr Val Ser Ser
            115                 120
```

<210> SEQ ID NO 44
<211> LENGTH: 98
<212> TYPE: PRT
<213> ORGANISM: human

<400> SEQUENCE: 44

```
Gln Val Gln Leu Val Glu Ser Gly Gly Val Val Gln Pro Gly Arg
 1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg
```

<210> SEQ ID NO 45
<211> LENGTH: 98
<212> TYPE: PRT

<213> ORGANISM: human

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Ser Gly Asp Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 46
<211> LENGTH: 111
<212> TYPE: PRT
<213> ORGANISM: human

<400> SEQUENCE: 46

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Ser Val Gln Trp Tyr Gln Gln Arg Pro Gly Ser Ala Pro Ile Thr Val
        35                  40                  45

Ile Tyr Glu Asp Thr Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Gln Thr Glu Asp Glu Ala Asp Tyr Tyr Cys Gln Ser Tyr Asp Ser
                85                  90                  95

Ala Tyr His Trp Val Phe Gly Gly Gly Thr Lys Leu Ala Val Leu
            100                 105                 110

<210> SEQ ID NO 47
<211> LENGTH: 98
<212> TYPE: PRT
<213> ORGANISM: human

<400> SEQUENCE: 47

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Tyr Glu Asp Asn Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn

<210> SEQ ID NO 48
<211> LENGTH: 331
<212> TYPE: PRT
<213> ORGANISM: human

<400> SEQUENCE: 48

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Asp
225                 230                 235                 240

Glu Leu Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 49
<211> LENGTH: 106
<212> TYPE: PRT
<213> ORGANISM: human

```
<400> SEQUENCE: 49

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 50
<211> LENGTH: 107
<212> TYPE: PRT
<213> ORGANISM: human

<400> SEQUENCE: 50

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 51
<211> LENGTH: 760
<212> TYPE: PRT
<213> ORGANISM: human

<400> SEQUENCE: 51

Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
            20                  25                  30

Asn Ser His Val Glu Met Lys Leu Ala Val Asp Glu Glu Asn Ala
        35                  40                  45

Asp Asn Asn Thr Lys Ala Asn Val Thr Lys Pro Lys Arg Cys Ser Gly
    50                  55                  60

Ser Ile Cys Tyr Gly Thr Ile Ala Val Ile Val Phe Phe Leu Ile Gly
65                  70                  75                  80

Phe Met Ile Gly Tyr Leu Gly Tyr Cys Lys Gly Val Glu Pro Lys Thr
                85                  90                  95

Glu Cys Glu Arg Leu Ala Gly Thr Glu Ser Pro Val Arg Glu Glu Pro
```

```
                100                 105                 110
Gly Glu Asp Phe Pro Ala Ala Arg Arg Leu Tyr Trp Asp Asp Leu Lys
            115                 120                 125

Arg Lys Leu Ser Glu Lys Leu Asp Ser Thr Asp Phe Thr Gly Thr Ile
130                 135                 140

Lys Leu Leu Asn Glu Asn Ser Tyr Val Pro Arg Glu Ala Gly Ser Gln
145                 150                 155                 160

Lys Asp Glu Asn Leu Ala Leu Tyr Val Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Arg
        195                 200                 205

Leu Val Tyr Leu Val Glu Asn Pro Gly Gly Tyr Val Ala Tyr Ser Lys
    210                 215                 220

Ala Ala Thr Val Thr Gly Lys Leu Val His Ala Asn Phe Gly Thr Lys
225                 230                 235                 240

Lys Asp Phe Glu Asp Leu Tyr Thr Pro Val Asn Gly Ser Ile Val Ile
                245                 250                 255

Val Arg Ala Gly Lys Ile Thr Phe Ala Glu Lys Val Ala Asn Ala Glu
            260                 265                 270

Ser Leu Asn Ala Ile Gly Val Leu Ile Tyr Met Asp Gln Thr Lys Phe
        275                 280                 285

Pro Ile Val Asn Ala Glu Leu Ser Phe Phe Gly His Ala His Leu Gly
    290                 295                 300

Thr Gly Asp Pro Tyr Thr Pro Gly Phe Pro Ser Phe Asn His Thr Gln
305                 310                 315                 320

Phe Pro Pro Ser Arg Ser Ser Gly Leu Pro Asn Ile Pro Val Gln Thr
                325                 330                 335

Ile Ser Arg Ala Ala Ala Glu Lys Leu Phe Gly Asn Met Glu Gly Asp
            340                 345                 350

Cys Pro Ser Asp Trp Lys Thr Asp Ser Thr Cys Arg Met Val Thr Ser
        355                 360                 365

Glu Ser Lys Asn Val Lys Leu Thr Val Ser Asn Val Leu Lys Glu Ile
    370                 375                 380

Lys Ile Leu Asn Ile Phe Gly Val Ile Lys Gly Phe Val Glu Pro Asp
385                 390                 395                 400

His Tyr Val Val Gly Ala Gln Arg Asp Ala Trp Gly Pro Gly Ala
                405                 410                 415

Ala Lys Ser Gly Val Gly Thr Ala Leu Leu Lys Leu Ala Gln Met
            420                 425                 430

Phe Ser Asp Met Val Leu Lys Asp Gly Phe Gln Pro Ser Arg Ser Ile
        435                 440                 445

Ile Phe Ala Ser Trp Ser Ala Gly Asp Phe Gly Ser Val Gly Ala Thr
    450                 455                 460

Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
                485                 490                 495

Ser Ala Ser Pro Leu Leu Tyr Thr Leu Ile Glu Lys Thr Met Gln Asn
            500                 505                 510

Val Lys His Pro Val Thr Gly Gln Phe Leu Tyr Gln Asp Ser Asn Trp
        515                 520                 525
```

-continued

```
Ala Ser Lys Val Glu Lys Leu Thr Leu Asp Asn Ala Ala Phe Pro Phe
            530                 535                 540
Leu Ala Tyr Ser Gly Ile Pro Ala Val Ser Phe Cys Phe Cys Glu Asp
545                 550                 555                 560
Thr Asp Tyr Pro Tyr Leu Gly Thr Thr Met Asp Thr Tyr Lys Glu Leu
                565                 570                 575
Ile Glu Arg Ile Pro Glu Leu Asn Lys Val Ala Arg Ala Ala Ala Glu
            580                 585                 590
Val Ala Gly Gln Phe Val Ile Lys Leu Thr His Asp Val Glu Leu Asn
            595                 600                 605
Leu Asp Tyr Glu Arg Tyr Asn Ser Gln Leu Leu Ser Phe Val Arg Asp
            610                 615                 620
Leu Asn Gln Tyr Arg Ala Asp Ile Lys Glu Met Gly Leu Ser Leu Gln
625                 630                 635                 640
Trp Leu Tyr Ser Ala Arg Gly Asp Phe Phe Arg Ala Thr Ser Arg Leu
                645                 650                 655
Thr Thr Asp Phe Gly Asn Ala Glu Lys Thr Asp Arg Phe Val Met Lys
            660                 665                 670
Lys Leu Asn Asp Arg Val Met Arg Val Glu Tyr His Phe Leu Ser Pro
            675                 680                 685
Tyr Val Ser Pro Lys Glu Ser Pro Phe Arg His Val Phe Trp Gly Ser
            690                 695                 700
Gly Ser His Thr Leu Pro Ala Leu Leu Glu Asn Leu Lys Leu Arg Lys
705                 710                 715                 720
Gln Asn Asn Gly Ala Phe Asn Glu Thr Leu Phe Arg Asn Gln Leu Ala
                725                 730                 735
Leu Ala Thr Trp Thr Ile Gln Gly Ala Ala Asn Ala Leu Ser Gly Asp
            740                 745                 750
Val Trp Asp Ile Asp Asn Glu Phe
            755                 760

<210> SEQ ID NO 52
<211> LENGTH: 17
<212> TYPE: PRT
<213> ORGANISM: human

<400> SEQUENCE: 52

Val Ile Ser Tyr Asp Gly Ser Ser Lys Tyr Tyr Ala Asp Ser Val Lys
1               5                   10                  15
Gly

<210> SEQ ID NO 53
<211> LENGTH: 17
<212> TYPE: PRT
<213> ORGANISM: human

<400> SEQUENCE: 53

Val Ile Ser Phe Asp Gly Ser Asn Lys Tyr Tyr Ala Asp Ser Val Lys
1               5                   10                  15
Gly

<210> SEQ ID NO 54
<211> LENGTH: 17
<212> TYPE: PRT
<213> ORGANISM: human

<400> SEQUENCE: 54
```

Val Ile Ser Tyr Asp Gly Ser Asn Lys Tyr Tyr Ala Asp Ser Val Lys
1               5                   10                  15
Gly

<210> SEQ ID NO 55
<211> LENGTH: 245
<212> TYPE: PRT
<213> ORGANISM: human

<400> SEQUENCE: 55

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Ser Phe Asn Thr Tyr
            20                  25                  30

Thr Met His Trp Val Arg Gln Ala Pro Gly Lys Gly Leu Glu Trp Val
        35                  40                  45

Ala Asp Ile Ala Tyr Asp Gly Ser Thr Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Val Ala Gly Glu Gly Tyr Phe Asp Leu Trp Gly Arg
            100                 105                 110

Gly Thr Leu Val Thr Val Ser Ser Gly Gly Gly Gly Ser Gly Gly Gly
        115                 120                 125

Gly Ser Gly Gly Gly Gly Ser Gln Ser Ala Leu Thr Gln Asp Pro Ala
    130                 135                 140

Val Ser Val Ala Leu Gly Gln Thr Val Arg Ile Thr Cys Gln Gly Asp
145                 150                 155                 160

Ser Leu Arg Ser Tyr Tyr Ala Ser Trp Tyr Gln Gln Leu Pro Gly Thr
                165                 170                 175

Ala Pro Lys Leu Leu Ile Tyr Arg Asn Asn Gln Arg Pro Ser Gly Val
            180                 185                 190

Pro Asp Arg Phe Ser Gly Ser Lys Ser Gly Thr Ser Ala Ser Leu Ala
        195                 200                 205

Ile Ser Gly Leu Arg Ser Glu Asp Glu Ala Asp Tyr Tyr Cys Ala Ala
    210                 215                 220

Trp Asp Asp Ser Leu Ser Ala Trp Val Phe Gly Gly Gly Thr Lys Leu
225                 230                 235                 240

Thr Val Leu Gly Ala
                245

<210> SEQ ID NO 56
<211> LENGTH: 735
<212> TYPE: DNA
<213> ORGANISM: human

<400> SEQUENCE: 56
caggtgcagc tgcaggagtc ggggggaggc ttggtacagc ctgggggtc cctgagactc      60 tcctgtgcag cctctggatt ctccttcaac acctatacta tgcactgggt ccgccaggct    120
ccaggcaagg ggctggagtg ggtggcggat atagcatatg atgggagtac taaatactac    180
gcagactctg tgaagggccg attcaccatc tccagagaca tgccaagaa ctcactgtat    240 ctgcaaatga acagcctgag agccgaggac acggctgtgt attactgtgc gagagatgca    300

```
gtggctggtg aagggtactt cgatctctgg ggccgtggca ccctggtcac cgtctcctca      360
ggtggaggcg gttcaggcgg aggtggctct ggcggtggcg gatcgcagtc tgctctgact      420
caggaccctg ctgtgtctgt ggccttggga cagacagtca ggatcacatg ccaaggagac      480
agcctcagaa gctattatgc aagttggtac cagcagctcc caggaacggc ccccaaactc      540
ctcatctata ggaataatca gcggccctca ggggtccctg accgattctc tggctccaag      600
tctggcacct cagcctccct ggccatcagt gggctccggt ccgaggatga ggctgattat      660
tactgtgcag catgggatga cagcctgagt gcctgggtgt cggcggagg gaccaagctg       720 accgtcctag gtgcg                                                       735
```

<210> SEQ ID NO 57
<211> LENGTH: 243
<212> TYPE: PRT
<213> ORGANISM: human

<400> SEQUENCE: 57

```
Gln Val Gln Leu Gln Glu Ser Gly Gly Gly Val Val Gln Pro Gly Arg
1               5                   10                  15

Ser Leu Arg Leu Ser Cys Ala Ala Ser Arg Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ser Gly Tyr Gly Asp Tyr Pro Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Gly Ser Ser Glu Leu Thr Gln Asp Pro Ala Val
    130                 135                 140

Ser Val Ala Leu Gly Gln Thr Val Arg Ile Thr Cys Gln Gly Asp Ser
145                 150                 155                 160

Leu Arg Ser Tyr Tyr Ala Ser Trp Tyr Gln Gln Lys Pro Gly Gln Ala
                165                 170                 175

Pro Val Leu Val Met Tyr Gly Arg Asn Glu Arg Pro Ser Gly Val Pro
            180                 185                 190

Asp Arg Phe Ser Gly Ser Lys Ser Gly Thr Ser Ala Ser Leu Ala Ile
        195                 200                 205

Ser Gly Leu Gln Pro Glu Asp Glu Ala Asn Tyr Tyr Cys Ala Gly Trp
    210                 215                 220

Asp Asp Ser Leu Thr Gly Pro Val Phe Gly Gly Gly Thr Lys Leu Thr
225                 230                 235                 240

Val Leu Gly
```

<210> SEQ ID NO 58
<211> LENGTH: 729
<212> TYPE: DNA
<213> ORGANISM: human

<400> SEQUENCE: 58

```
caggtgcagc tgcaggagtc ggggggaggc gtggtccagc ctggggaggtc cctgagactc      60 tcctgtgcag cctctcgatt caccttcagt agctatgcta tgcactgggt ccgccaggct     120
ccaggcaagg ggctggagtg ggtggcagtt atatcatatg atggaagcaa taaatactac     180
gcagactccg tgaagggccg attcaccatc tccagagaca attccaagaa cacgctgtat     240
ctgcaaatga acagcctgag agctgaggac acggctgtgt attactgtgc gagagatctc     300
tcggggtacg gtgactaccc tgactactgg ggccagggaa ccctggtcac cgtctcctca     360
ggtggaggcg gttcaggcgg aggtggctct ggcggtggcg gatcgtctga gctgactcag     420
gaccctgctg tgtctgtggc cttgggacag acagtcagaa tcacatgcca aggagacagc     480
ctcagaagct attatgcaag ctggtaccag cagaagccag gacaggcccc tgtacttgtc     540
atgtatggta aaacgagcg gccctcaggg gttcctgacc gattctctgg ctccaagtct     600
ggcacctctg cctccctggc atcagtggc ctccagccag aggatgaggc taattattac     660 tgtgcaggg tgggatgacag cctgactggt ccggtgttcg gcggagggac caagctgacc     720
gtcctaggt                                                             729

<210> SEQ ID NO 59
<211> LENGTH: 120
<212> TYPE: PRT
<213> ORGANISM: human

<400> SEQUENCE: 59

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Ser Phe Asn Thr Tyr
            20                  25                  30

Thr Met His Trp Val Arg Gln Ala Pro Gly Lys Gly Leu Glu Trp Val
        35                  40                  45

Ala Asp Ile Ala Tyr Asp Gly Ser Thr Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Val Ala Gly Glu Gly Tyr Phe Asp Leu Trp Gly Arg
            100                 105                 110

Gly Thr Leu Val Thr Val Ser Ser
        115                 120

<210> SEQ ID NO 60
<211> LENGTH: 360
<212> TYPE: DNA
<213> ORGANISM: human

<400> SEQUENCE: 60
caggtgcagc tgcaggagtc ggggggaggc ttggtacagc ctggggggtc cctgagactc      60
tcctgtgcag cctctggatt ctccttcaac acctatacta tgcactgggt ccgccaggct     120
ccaggcaagg ggctggagtg ggtggcgat atagcatatg atgggagtac taaatactac     180
gcagactctg tgaagggccg attcaccatc tccagagaca atgccaagaa ctcactgtat     240
ctgcaaatga acagcctgag agccgaggac acggctgtgt attactgtgc gagagatgca     300
gtggctggtg aagggtactt cgatctctgg ggccgtggca ccctggtcac cgtctcctca     360
```

<210> SEQ ID NO 61
<211> LENGTH: 120
<212> TYPE: PRT
<213> ORGANISM: human

<400> SEQUENCE: 61

Gln Val Gln Leu Gln Glu Ser Gly Gly Gly Val Val Gln Pro Gly Arg
1               5                   10                  15

Ser Leu Arg Leu Ser Cys Ala Ala Ser Arg Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ser Gly Tyr Gly Asp Tyr Pro Asp Tyr Trp Gly Gln
            100                 105                 110

Gly Thr Leu Val Thr Val Ser Ser
        115                 120

<210> SEQ ID NO 62
<211> LENGTH: 360
<212> TYPE: DNA
<213> ORGANISM: human

<400> SEQUENCE: 62
caggtgcagc tgcaggagtc ggggggaggc gtggtccagc ctgggaggtc cctgagactc      60
tcctgtgcag cctctcgatt caccttcagt agctatgcta tgcactgggt ccgccaggct     120
ccaggcaagg ggctggagtg ggtggcagtt atatcatatg atggaagcaa taaatactac     180
gcagactccg tgaagggccg attcaccatc tccagagaca attccaagaa cacgctgtat     240
ctgcaaatga acagcctgag agctgaggac acggctgtgt attactgtgc gagagatctc     300
tcggggtacg gtgactaccc tgactactgg ggccagggaa ccctggtcac cgtctcctca     360

<210> SEQ ID NO 63
<211> LENGTH: 108
<212> TYPE: PRT
<213> ORGANISM: human

<400> SEQUENCE: 63

Gln Ser Ala Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Leu Pro Gly Thr Ala Pro Lys Leu Leu Ile Tyr
        35                  40                  45

Arg Asn Asn Gln Arg Pro Ser Gly Val Pro Asp Arg Phe Ser Gly Ser
    50                  55                  60

Lys Ser Gly Thr Ser Ala Ser Leu Ala Ile Ser Gly Leu Arg Ser Glu
65                  70                  75                  80

Asp Glu Ala Asp Tyr Tyr Cys Ala Ala Trp Asp Asp Ser Leu Ser Ala
                85                  90                  95

Trp Val Phe Gly Gly Gly Thr Lys Leu Thr Val Leu

<210> SEQ ID NO 64
<211> LENGTH: 324
<212> TYPE: DNA
<213> ORGANISM: human

<400> SEQUENCE: 64

```
cagtctgctc tgactcagga ccctgctgtg tctgtggcct tgggacagac agtcaggatc    60
acatgccaag gagacagcct cagaagctat tatgcaagtt ggtaccagca gctcccagga   120
acggccccca aactcctcat ctataggaat aatcagcggc cctcaggggt ccctgaccga   180
ttctctggct ccaagtctgg cacctcagcc tccctggcca tcagtgggct ccggtccgag   240
gatgaggctg attattactg tgcagcatgg gatgacagcc tgagtgcctg gtgttcggc    300
ggagggacca agctgaccgt ccta                                         324
```

<210> SEQ ID NO 65
<211> LENGTH: 106
<212> TYPE: PRT
<213> ORGANISM: human

<400> SEQUENCE: 65

```
Glu Leu Thr Gln Asp Pro Ala Val Ser Val Ala Leu Gly Gln Thr Val
1               5                   10                  15
Arg Ile Thr Cys Gln Gly Asp Ser Leu Arg Ser Tyr Tyr Ala Ser Trp
            20                  25                  30
Tyr Gln Gln Lys Pro Gly Gln Ala Pro Val Leu Val Met Tyr Gly Arg
        35                  40                  45
Asn Glu Arg Pro Ser Gly Val Pro Asp Arg Phe Ser Gly Ser Lys Ser
    50                  55                  60
Gly Thr Ser Ala Ser Leu Ala Ile Ser Gly Leu Gln Pro Glu Asp Glu
65                  70                  75                  80
Ala Asn Tyr Tyr Cys Ala Gly Trp Asp Asp Ser Leu Thr Gly Pro Val
                85                  90                  95
Phe Gly Gly Gly Thr Lys Leu Thr Val Leu
            100                 105
```

<210> SEQ ID NO 66
<211> LENGTH: 318
<212> TYPE: DNA
<213> ORGANISM: human

<400> SEQUENCE: 66

```
gagctgactc aggaccctgc tgtgtctgtg gccttgggac agacagtcag aatcacatgc    60
caaggagaca gcctcagaag ctattatgca agctggtacc agcagaagcc aggacaggcc   120
cctgtacttg tcatgtatgg tagaaacgag cggccctcag ggttcctga ccgattctct    180
ggctccaagt ctggcacctc tgcctccctg gccatcagtg gcctccagcc agaggatgag   240
gctaattatt actgtgcagg gtgggatgac agcctgactg gtccggtgtt cggcggaggg   300
accaagctga ccgtccta                                                318
```

<210> SEQ ID NO 67
<211> LENGTH: 106
<212> TYPE: PRT
<213> ORGANISM: humnan

<400> SEQUENCE: 67

```
Gly Gln Pro Lys Ala Ala Pro Ser Val Thr Leu Phe Pro Pro Ser Ser
  1               5                  10                  15

Glu Glu Leu Gln Ala Asn Lys Ala Thr Leu Val Cys Leu Ile Ser Asp
             20                  25                  30

Phe Tyr Pro Gly Ala Val Thr Val Ala Trp Lys Ala Asp Ser Ser Pro
         35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Lys Ser Tyr Ser Cys Gln Val Thr His Glu Gly Ser Thr Val
             85                  90                  95

Glu Lys Thr Val Ala Pro Thr Glu Cys Ser
            100                 105
```

<210> SEQ ID NO 68
<211> LENGTH: 321
<212> TYPE: DNA
<213> ORGANISM: human

<400> SEQUENCE: 68

```
ggtcagccca aggctgcccc ctcggtcact ctgttcccac cctcctctga ggagcttcaa    60
gccaacaagg ccacactggt gtgtctcata agtgacttct acccgggagc cgtgacagtt   120
gcctggaagg cagatagcag ccccgtcaag gcggggggtgg agaccaccac ccctccaaa   180
caaagcaaca caagtacgc ggccagcagc tacctgagcc tgacgcctga gcagtggaag   240
tcccacaaaa gctacagctg ccaggtcacg catgaaggga gcaccgtgga agacagtt   300
gcccctacgg aatgttcata g                                            321
```

<210> SEQ ID NO 69
<211> LENGTH: 120
<212> TYPE: PRT
<213> ORGANISM: human

<400> SEQUENCE: 69

```
Gln Val Gln Leu Gln Glu Ser Gly Gly Gly Leu Val Gln Pro Gly Gly
  1               5                  10                  15

Ser Leu Arg Leu Ser Cys Ala Ala Ser Gly Phe Ser Phe Asn Thr Tyr
             20                  25                  30

Thr Met His Trp Val Arg Gln Ala Pro Gly Lys Gly Leu Glu Trp Val
         35                  40                  45

Ala Asp Ile Ala Tyr Asp Gly Ser Thr Lys Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
             85                  90                  95

Ala Arg Asp Ala Val Ala Gly Glu Gly Tyr Phe Asp Leu Trp Gly Arg
            100                 105                 110

Gly Thr Leu Val Thr Val Ser Ser
            115                 120
```

<210> SEQ ID NO 70
<211> LENGTH: 360
<212> TYPE: DNA
<213> ORGANISM: Artificial Sequence
<220> FEATURE:

<223> OTHER INFORMATION: Description of Artificial Sequence: optimized
    nucleotide sequence

<400> SEQUENCE: 70
caagttcaac tacaagaatc cggcggcggc ctggtgcagc ccggcggctc cctgaggctg    60
tcctgcgccg cctccggctt ctccttcaac acctacacca tgcactgggt caggcaggcc   120
cccggcaagg gcctggagtg ggtggccgac atcgcctacg acggctccac caagtactac   180
gccgactccg tgaagggcag gttcaccatc tccaggaca cgccaagaa ctccctgtac    240 ctgcagatga actccctgag ggccgaggac accgccgtgt actactgcgc cagggacgcc   300
gtggccggcg agggctactt cgacctgtgg ggcaggggca ccctggtgac cgtgtcctcc   360

<210> SEQ ID NO 71
<211> LENGTH: 214
<212> TYPE: PRT
<213> ORGANISM: human

<400> SEQUENCE: 71

Gln Ser Ala Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Leu Pro Gly Thr Ala Pro Lys Leu Leu Ile Tyr
        35                  40                  45

Arg Asn Asn Gln Arg Pro Ser Gly Val Pro Asp Arg Phe Ser Gly Ser
    50                  55                  60

Lys Ser Gly Thr Ser Ala Ser Leu Ala Ile Ser Gly Leu Arg Ser Glu
65                  70                  75                  80

Asp Glu Ala Asp Tyr Tyr Cys Ala Ala Trp Asp Asp Ser Leu Ser Ala
                85                  90                  95

Trp Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Lys Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 72
<211> LENGTH: 645
<212> TYPE: DNA
<213> ORGANISM: Artificial Sequence
<220> FEATURE:
<223> OTHER INFORMATION: Description of Artificial Sequence: optimized
    nucleotide sequence

<400> SEQUENCE: 72
caatcagcac taacacaaga ccccgccgtg tccgtggccc tgggccagac cgtgaggatc    60

```
acctgccagg gcgactccct gaggtcctac tacgcctcct ggtaccagca gctgcccggc    120
accgccccca agctgctgat ctaccgcaac aaccagaggc cctccggcgt gcccgaccgc    180
ttctccggct ccaagtccgg cacctccgcc tccctggcca tctccggcct gaggtccgag    240
gacgaggccg actactactg cgccgcctgg gacgactccc tgtccgcctg ggtgttcggc    300
ggcggcacca agctgaccgt gctgggccag cccaaggccg cccctccgt gaccctgttc     360 ccccctcct ccgaggagct gcaggccaac aaggccaccc tggtgtgcct gatctccgac     420
ttctaccccg gcgccgtgac cgtggcctgg aaggccgact cctccccgt gaaggccggc     480 gtggagacca ccaccccctc caagcagtcc aacaacaaat acgccgcctc ctcctacctg    540
tccctgaccc ccgagcagtg gaagtcccac aagtcctact cctgccaagt cacccacgag    600
ggctccaccg tggagaagac cgtggccccc accgagtgct cctga                    645
```

<210> SEQ ID NO 73
<211> LENGTH: 120
<212> TYPE: PRT
<213> ORGANISM: human

<400> SEQUENCE: 73

```
Gln Val Gln Leu Gln Glu Ser Gly Gly Gly Val Val Gln Pro Gly Arg
1               5                   10                  15

Ser Leu Arg Leu Ser Cys Ala Ala Ser Arg Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ser Gly Tyr Gly Asp Tyr Pro Asp Tyr Trp Gly Gln
            100                 105                 110

Gly Thr Leu Val Thr Val Ser Ser
        115                 120
```

<210> SEQ ID NO 74
<211> LENGTH: 360
<212> TYPE: DNA
<213> ORGANISM: Artificial Sequence
<220> FEATURE:
<223> OTHER INFORMATION: Description of Artificial Sequence: optimized
    nucleotide sequence

<400> SEQUENCE: 74

```
caagttcaac tacaagaatc cggcggcggc gtggtgcagc ccggcaggtc cctgaggctg    60
tcctgcgccg cctcccgctt caccttctcc tcctacgcca tgcactgggt ccgccaagcc    120
cccggcaagg gcctggagtg ggtggccgtg atctcctacg acggctccaa caagtactac    180
gccgactcct gaagggcag gttcaccatc tccaggaca ctccaagaa cacccctgtac     240 ctgcagatga actccctgag gccgaggac accgccgtgt actactgcgc cagggacctg    300
tccggctacg gcgactaccc cgactactgg ggccagggca ccctggtgac cgtgtcctcc    360
```

<210> SEQ ID NO 75
<211> LENGTH: 212

<212> TYPE: PRT
<213> ORGANISM: human

<400> SEQUENCE: 75

```
Glu Leu Thr Gln Asp Pro Ala Val Ser Val Ala Leu Gly Gln Thr Val
1               5                   10                  15
Arg Ile Thr Cys Gln Gly Asp Ser Leu Arg Ser Tyr Tyr Ala Ser Trp
            20                  25                  30
Tyr Gln Gln Lys Pro Gly Gln Ala Pro Val Leu Val Met Tyr Gly Arg
        35                  40                  45
Asn Glu Arg Pro Ser Gly Val Pro Asp Arg Phe Ser Gly Ser Lys Ser
    50                  55                  60
Gly Thr Ser Ala Ser Leu Ala Ile Ser Gly Leu Gln Pro Glu Asp Glu
65                  70                  75                  80
Ala Asn Tyr Tyr Cys Ala Gly Trp Asp Asp Ser Leu Thr Gly Pro Val
                85                  90                  95
Phe Gly Gly Gly Thr Lys Leu Thr Val Leu Gly Gln Pro Lys Ala Ala
            100                 105                 110
Pro Ser Val Thr Leu Phe Pro Pro Ser Ser Glu Glu Leu Gln Ala Asn
        115                 120                 125
Lys Ala Thr Leu Val Cys Leu Ile Ser Asp Phe Tyr Pro Gly Ala Val
    130                 135                 140
Thr Val Ala Trp Lys Ala Asp Ser Ser Pro Val Lys Ala Gly Val Glu
145                 150                 155                 160
Thr Thr Thr Pro Ser Lys Gln Ser Asn Asn Lys Tyr Ala Ala Ser Ser
                165                 170                 175
Tyr Leu Ser Leu Thr Pro Glu Gln Trp Lys Ser His Lys Ser Tyr Ser
            180                 185                 190
Cys Gln Val Thr His Glu Gly Ser Thr Val Glu Lys Thr Val Ala Pro
        195                 200                 205
Thr Glu Cys Ser
    210
```

<210> SEQ ID NO 76
<211> LENGTH: 639
<212> TYPE: DNA
<213> ORGANISM: Artificial Sequence
<220> FEATURE:
<223> OTHER INFORMATION: Description of Artificial Sequence: optimized nucleotide sequence

<400> SEQUENCE: 76

```
gaactaacac aagatccagc cgtgtccgtg ccctgggcc agaccgtgag gatcacctgc       60
cagggcgact ccctgaggtc ctactacgcc tcctggtacc agcagaagcc cggccaggcc     120
cccgtgctgg tgatgtacgg caggaacgag aggccctccg gcgtgcccga ccgcttctcc     180
ggctccaagt ccggcaccct cgcctcccctg gccatctccg gcctgcagcc cgaggacgag    240
gccaactact actgcgccgg ctgggacgac tccctgaccg gccccgtgtt cggcggcggc     300
accaagctga ccgtgctggg ccagcccaag gccgccccct ccgtgaccct gttcccccc      360
tcctccgagg agctgcaggc caacaaggcc accctggtgt gcctgatctc cgacttctac     420
cccggcgccg tgaccgtggc ctggaaggcc gactcctccc ccgtgaaggc cggcgtggag     480
accaccaccc cctccaagca gtccaacaac aaatacgccg cctcctccta cctgtccctg     540
accccccgagc agtggaagtc ccacaagtcc tactcctgcc aagtcaccca cgagggctcc    600
accgtggaga agaccgtggc ccccaccgag tgctcctga                           639
```

<210> SEQ ID NO 77
<211> LENGTH: 330
<212> TYPE: PRT
<213> ORGANISM: human

<400> SEQUENCE: 77

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 78
<211> LENGTH: 993
<212> TYPE: DNA
<213> ORGANISM: human

<400> SEQUENCE: 78

```
gcctccacca agggccccto cgtgttcccc ctggcccoct cctccaagtc cacctccggc     60
ggcaccgccg ccctgggctg cctggtgaag gactacttcc ccgagcccgt gaccgtgtcc    120
tggaactccg gcgccctgac ctccggcgtg cacaccttcc ccgccgtgct gcagtcctcc    180
ggcctgtact ccctgtcctc cgtggtgacc gtgccctcct cctccctggg cacccagacc    240
tacatctgca acgtgaacca caagccctcc aacaccaagg tggacaagaa ggtggagccc    300
aagtcctgcg acaagaccca cacctgcccc cctgccccg cccccgagct gctgggcggc     360
ccctccgtgt tcctgttccc ccccaagccc aaggacaccc tgatgatctc ccgcaccccc    420
gaggtgacct gcgtggtggt ggacgtgtcc cacgaggacc ccgaggtgaa gttcaactgg    480
tacgtggacg gcgtggaggt gcacaacgcc aagaccaagc ccagggagga gcagtacaac    540
tccacctaca gggtggtgtc cgtgctgacc gtgctgcacc aggactggct gaacggcaag    600
gagtacaagt gcaaggtgtc caacaaggcc ctgcccgccc ccatcgagaa gaccatctcc    660
aaggccaagg gccagcccag ggagccccag gtgtacaccc tgccccctc ccgcgacgag     720 ctgaccaaga accaggtgtc cctgacctgc ctggtgaagg gcttctaccc ctccgacatc    780
gccgtggagt gggagtccaa cggccagccc gagaacaact acaagaccac ccccccgtg     840 ctggactccg acggctcctt cttcctgtac tccaagctga ccgtggacaa gtccaggtgg    900
cagcagggca acgtgttctc ctgctccgtg atgcacgagg ccctgcacaa ccactacacc    960
cagaagtccc tgtccctgtc ccccggcaag tga                                 993
```